(12) United States Patent
Walter et al.

(10) Patent No.: US 7,109,150 B2
(45) Date of Patent: *Sep. 19, 2006

(54) TRIFLUOROMETHYLPYRROLECARBOXAMIDES AND TRIFLUOROMETHYL-PYRROLETHIOAMIDES AS FUNGICIDES

(75) Inventors: Harald Walter, Basel (CH); Stephan Trah, Basel (CH); Hermann Schneider, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/785,836

(22) Filed: Feb. 24, 2004

(65) Prior Publication Data

US 2004/0171490 A1    Sep. 2, 2004

Related U.S. Application Data

(62) Division of application No. 10/169,281, filed as application No. PCT/EP00/11196 on Nov. 11, 2000, now Pat. No. 6,699,818.

(30) Foreign Application Priority Data

Dec. 29, 1999    (GB) ............................. 9930750.6

(51) Int. Cl.
A01N 43/40    (2006.01)
C07D 401/12   (2006.01)

(52) U.S. Cl. .................................... 504/252; 546/279.1

(58) Field of Classification Search ............... 548/537, 548/527, 249; 546/281.4, 279.1; 504/287
See application file for complete search history.

(56) References Cited

U.S. PATENT DOCUMENTS

| | | | |
|---|---|---|---|
| 5,162,308 A | 11/1992 | Brown et al. | |
| 5,438,070 A | 8/1995 | Eicken et al. | |
| 6,365,620 B1 * | 4/2002 | Eberle et al. | 514/422 |
| 6,806,286 B1 * | 10/2004 | Walter et al. | 514/423 |
| 2004/0039043 A1 * | 2/2004 | Elbe et al. | 514/406 |
| 2004/0082477 A1 * | 4/2004 | Walter | 504/287 |
| 2004/0106521 A1 * | 6/2004 | Walter et al. | 504/271 |
| 2004/0138265 A1 * | 7/2004 | Walter et al. | 514/337 |
| 2005/0119130 A1 * | 6/2005 | Walter | 504/287 |

FOREIGN PATENT DOCUMENTS

| | | |
|---|---|---|
| EP | 0 372 263 | 6/1990 |
| EP | 0 481 182 | 4/1992 |
| EP | 0 566 138 | 10/1993 |
| EP | 0 600 157 | 8/1994 |
| EP | 0 737 682 | 10/1996 |
| WO | WO 97 08148 | 3/1997 |
| WO | WO 00 09482 | 1/2000 |

* cited by examiner

Primary Examiner—Kamal A. Saeed
Assistant Examiner—Jason M. Nolan
(74) Attorney, Agent, or Firm—Rebecca Gegick

(57) ABSTRACT

Novel pyrrole derivatives of formula I

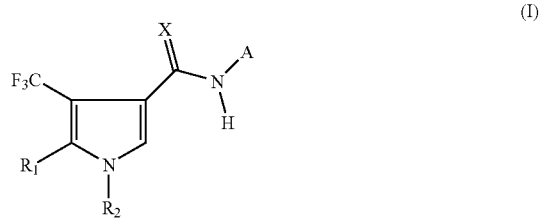

wherein
X is oxygen or sulfur;
$R_1$ is hydrogen, $C_1$–$C_4$alkyl unsubstituted or substituted, or halogen;
$R_2$ is $C_1$–$C_4$alkyl unsubstituted or substituted; and
A is orthosubstituted aryl; orthosubstituted heteroaryl; bicycloaryl unsubstituted or substituted; or bicycloheteroaryl unsubstituted or substituted.

The novel compounds have plant-protective properties and are suitable for protecting plants against infestations by phytopathogenic microorganisms.

11 Claims, No Drawings

TRIFLUOROMETHYLPYRROLECARBOXAMIDES AND TRIFLUOROMETHYLPYRROLETHIOAMIDES AS FUNGICIDES

This application is a division of U.S. patent application Ser. No. 10/169,281, filed Oct. 8, 2002, now U.S. Pat. No. 6,699,818, which is the National Stage of International Application No. PCT/EP00/11196, filed Nov. 11, 2000

The present invention relates to novel trifluoromethylpyrrolecarboxamides or trifluoromethylpyrrolethioamides which have microbicidal activity, in particular fungicidal activity. The invention also relates to the preparation of these substances, to agrochemical compositions which comprise at least one of the novel compounds as active ingredient, to the preparation of the compositions mentioned and to the use of the active ingredients or compositions in agriculture and horticulture for controlling or preventing infestation of plants by phytopathogenic microorganisms, preferably fungi.

The trifluoromethylpyrrolecarboxamides of the present invention have the general formula I

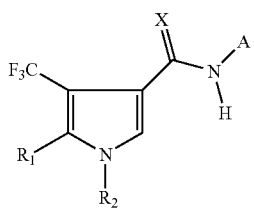

(I)

wherein

X is oxygen or sulfur;

$R_1$ is hydrogen, $C_1$–$C_4$alkyl unsubstituted or substituted, $C_1$–$C_4$alkoxy unsubstituted or substituted, or halogen;

$R_2$ is $C_1$–$C_4$alkyl unsubstituted or substituted; and

A is orthosubstituted aryl; orthosubstituted heteroaryl; bicycloaryl unsubstituted or substituted; or bicycloheteroaryl unsubstituted or substituted.

Surprisingly, it has now been found that the compounds of formula I exhibit improved biological properties which render them more suitable for the practical use in agriculture and horticulture.

Where asymmetrical carbon atoms are present in the compounds of formula I, these compounds are in optically active form. The invention relates to the pure isomers, such as enantiomers and diastereomers, as well as to all possible mixtures of isomers, e.g. mixtures of diastereomers, racemates or mixture of racemates.

Within the present specification alkyl denotes methyl, ethyl, n-propyl, isopropyl, n-butyl, sec-butyl, isobutyl and tert-butyl. Non-branched alkyl is preferred. Alkyl as part of other radicals such as alkoxy, haloalkyl, alkylcycloalkyl, alkylcycloalkoxy, etc. is understood in an analogous way. Halogen will be understood generally as meaning fluoro, chloro, bromo or iodo. Fluoro, chloro or bromo are preferred meanings. Halogen as part of other radicals such as haloalkyl, haloalkoxy, haloalkenyl, haloalkenyloxy, haloaryl or haloheteroaryl, etc. is understood in an analogous way. Haloaryl or haloheteroaryl designates mono- to five times halo-substituted aryl, whereby the halogens are independently chosen. Where more than two halogens are present, the halogens are preferably the same, e.g. trifluorophenyl, trichlorophenyl, tetrachlorophenyl or perchlorophenyl.

Aryl is phenyl or naphthyl.

Heteroaryl will be understood as a 5- to 10-membered ring that may contain up to 3 heteroatoms, such as nitrogen, oxygen or sulfur. The following list of examples is not exhaustive: furyl, thienyl, imidazolyl, pyrazolyl, thiazolyl, isothiazolyl, oxazolyl, isoxazolyl, oxadiazolyl, thiadiazolyl, triazolyl, tetrazolyl, pyrrolyl, dithiolyl, oxathiolyl, dioxazolyl, oxathiazolyl, oxathiolyl, pyridyl, pyridazinyl, pyrimidinyl, pyrazinyl, triazinyl, indolyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl, naphthyridinyl, isobenzofuranyl, isoindolyl, benzothiadiazolyl, benzothienyl, benzisoxazolyl, purinyl, 5,6-dihydro-1,4,2-dioxazinyl, and the like.

Bicycloaryl or bicycloheteroaryl will be understood as a 6-membered aryl or 6-membered heteroaryl, wherein it may contain up to 3 heteroatoms such as nitrogen, oxygen or sulfur, and which is fused to an additional ring. The fused ring may be aromatic, partially hydrogenated or completely saturated, may be a ring from 5 to 7 ring members, of which up to 3 members may be heteroatoms selected from the group nitrogen, oxygen and sulfur. The following list of examples is not exhaustive: dihydroisobenzofuranyl, dihydroisoindolyl, and the like.

Preferred embodiments of compounds of the formula I are those wherein

X is oxygen or sulfur; or

X is oxygen; or

X is sulfur; or $R_1$ is hydrogen, $C_1$–$C_4$alkyl unsubstituted or substituted, $C_1$–$C_4$alkoxy unsubstituted or substituted, or halogen; or $R_1$ is hydrogen, $C_1$–$C_4$alkyl, $C_1$–$C_4$haloalkyl, $C_1$–$C_4$alkoxy-$C_1$–$C_4$alkyl, $C_1$–$C_4$alkoxy, $C_1$–$C_4$haloalkoxy, $C_1$–$C_4$haloalkoxy-$C_1$–$C_4$alkyl or halogen; or $R_1$ is hydrogen, $C_1$–$C_4$alkyl or $C_1$–$C_4$haloalkyl; or $R_1$ is hydrogen or $C_1$–$C_3$alkyl; or $R_2$ is $C_1$–$C_4$alkyl unsubstituted or substituted; or $R_2$ is $C_1$–$C_4$alkyl, $C_1$–$C_4$haloalkyl, $C_1$–$C_4$alkoxy-$C_1$–$C_4$alkyl or $C_1$–$C_4$haloalkoxy-$C_1$–$C_4$alkyl; or $R_2$ is $C_1$–$C_4$alkyl, $C_1$–$C_3$haloalkyl or $C_1$–$C_3$alkoxy-$C_1$–$C_3$alkyl; or $R_2$ is $C_1$–$C_3$alkyl or $C_1$–$C_3$alkoxy-$C_1$–$C_3$alkyl; or A is orthosubstituted aryl; orthosubstituted heteroaryl; bicycloaryl unsubstituted or substituted; or bicycloheteroaryl unsubstituted or substituted; or A is a group

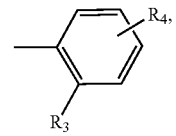

(A1)

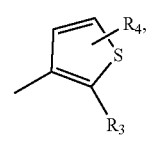

(A2)

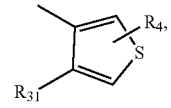

(A3)

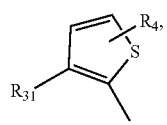 (A4)
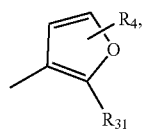 (A5)
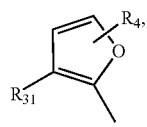 (A6)
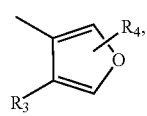 (A7)
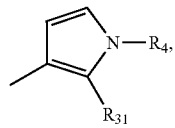 (A8)
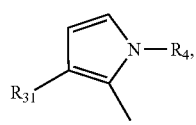 A(9)
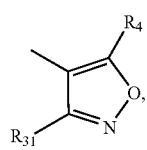 (A10)
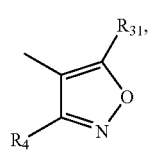 (A11)
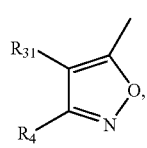 (A12)
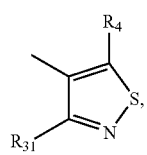 (A13)
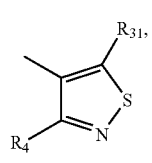 (A14)
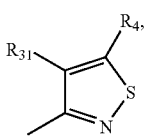 (A15)
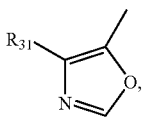 (A16)
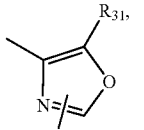 (A17)
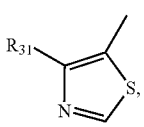 (A18)
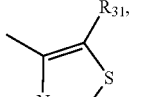 (A19)
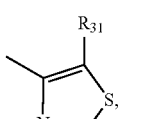 (A20)
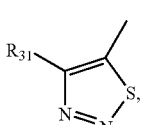 (A21)
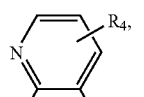 (A22)
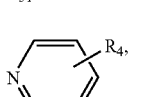 (A23)
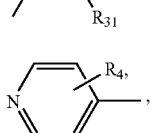 (A24)
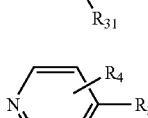 (A25)

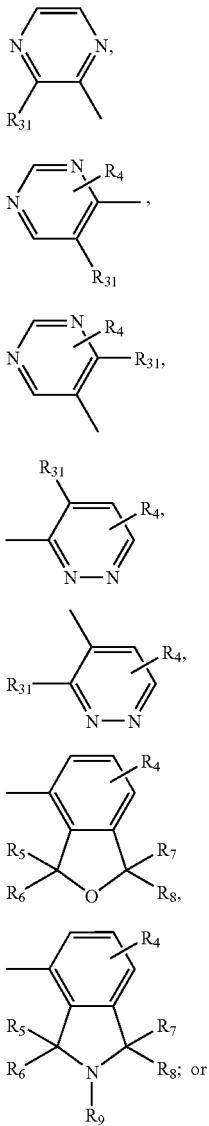

A is A1, A2, A3, A5, A8, A10, A13, A14, A17, A18, A20, A21, A22, A24, A25, A26, A27, A29, A31 or A32; or

A is A1, A2, A3, A17, A20, A21, A24, A25, A26, A27 or A31; or $R_3$ is $C_3$–$C_7$cycloalkyl unsubstituted or mono- to trisubstituted by halogen, hydroxy, $C_1$–$C_4$alkoxy, $C_1$–$C_4$haloalkyl, $C_2$–$C_4$alkenyl, $C_2$–$C_4$alkynyl, $C_1$–$C_4$haloalkoxy or $C_1$–$C_4$alkyl;

$C_4$–$C_7$cycloalkenyl unsubstituted or mono- to trisubstituted by halogen, hydroxy, $C_1$–$C_4$alkoxy, $C_1$–$C_4$haloalkyl, $C_2$–$C_4$alkenyl, $C_2$–$C_4$alkynyl, $C_1$–$C_4$haloalkoxy or $C_1$–$C_4$alkyl; $C_6$–$C_7$cyclodialkenyl unsubstituted or mono- to trisubstituted by halogen, hydroxy, $C_1$–$C_4$alkoxy, $C_1$–$C_4$haloalkyl, $C_2$–$C_4$alkenyl, $C_2$–$C_4$alkynyl, $C_1$–$C_4$haloalkoxy or $C_1$–$C_4$alkyl; thienyl, furyl, pyrrolyl, pyrazolyl, oxazolyl, thiazolyl, isoxazolyl, isothiazolyl, thiadiazolyl, imidazolyl, tetrazolyl, triazinyl, benzothienyl, 5,6-dihydro-1,4,2-dioxazinyl, pyridyl, pyrazinyl, pyridazinyl or pyrimidinyl, which are unsubstituted or substituted by halogen, $C_1$–$C_6$haloalkyl, $C_1$–$C_6$alkyl, hydroxy, cyano, nitro, CHO, $C_1$–$C_4$alkoxy-$C_1$–$C_4$alkyl, $COOC_1$–$C_4$alkyl, $C_1$–$C_6$haloalkoxy-$C_1$–$C_4$alkyl, $C_1$–$C_6$alkoxy or $C_1$–$C_6$haloalkoxy; or $R_3$ is $C_5$–$C_7$cycloalkyl unsubstituted or mono- to trisubstituted by halogen, hydroxy, $C_2$–$C_4$alkenyl, $C_2$–$C_4$alkynyl, $C_1$–$C_3$alkoxy or $C_1$–$C_4$alkyl; $C_5$–$C_7$cycloalkenyl unsubstituted or mono- to trisubstituted by halogen, hydroxy, $C_1$–$C_3$alkoxy, $C_2$–$C_4$alkenyl, $C_2$–$C_4$alkynyl or $C_1$–$C_4$alkyl; $C_6$–$C_7$cyclodialkenyl unsubstituted or mono- to trisubstituted by halogen, hydroxy, $C_1$–$C_3$alkoxy, $C_2$–$C_4$alkenyl, $C_2$–$C_4$alkynyl or $C_1$–$C_3$alkyl; thienyl, furyl, oxazolyl, isoxazolyl, thiadiazolyl, triazinyl, pyridyl, pyrazinyl, pyridazinyl or pyrimidinyl, which are unsubstituted or substituted by halogen, $C_1$–$C_4$haloalkyl, $C_1$–$C_4$alkyl, hydroxy, $C_1$–$C_4$alkoxy or $C_1$–$C_4$haloalkoxy; or $R_3$ is cyclohexyl, cyclohexenyl or cyclohexadienyl, which are unsubstituted or mono- to disubstituted by chloro, bromo, $C_1$–$C_2$alkyl, $C_1$–$C_2$haloalkyl or $C_1$–$C_2$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy; or $R_{31}$ is $C_3$–$C_7$cycloalkyl, $C_3$–$C_7$cycloalkenyl or $C_5$–$C_7$cycloalkadienyl which are unsubstituted or substituted by halogen, $C_1$–$C_6$alkoxy, $C_1$–$C_6$alkoxy-$C_1$–$C_6$alkyl, $C_1$–$C_6$haloalkoxy-$C_1$–$C_4$alkyl, $C_1$–$C_4$alkyl, $C_1$–$C_4$haloalkyl, $C_1$–$C_4$haloalkoxy, $C_2$–$C_4$alkenyl or $C_2$–$C_5$alkynyl; phenyl unsubstituted or substituted by halogen, $C_1$–$C_6$alkoxy, $C_1$–$C_6$haloalkoxy, $C_1$–$C_4$alkyl, $C_1$–$C_4$haloalkyl, $C_2$–$C_4$alkenyl, $C_2$–$C_5$ alkynyl, CHO, $COOC_1$–$C_4$alkyl, $C_1$–$C_4$alkoxy-$C_1$–$C_4$alkyl, $C_1$–$C_4$alkyl-$C_1$–$C_4$alkoxy, $C_1$–$C_4$haloalkoxy-$C_1$–$C_4$alkyl, $C_1$–$C_4$haloalkyl-$C_1$–$C_4$alkoxy, cyano or nitro; thienyl, furyl, pyrrolyl, pyrazolyl, oxazolyl, thiazolyl, isoxazolyl, isothiazolyl, thiadiazolyl, imidazolyl, triazinyl, pyridyl, pyridazinyl, pyrazinyl or pyrimidinyl, which are unsubstituted or substituted by halogen, $C_1$–$C_6$haloalkyl, $C_1$–$C_6$alkyl, hydroxy, cyano, nitro, CHO, $COOC_1$–$C_4$alkyl, $C_1$–$C_6$haloalkoxy-$C_1$–$C_4$alkyl, $C_1$–$C_4$alkoxy-$C_1$–$C_4$alkyl, $C_1$–$C_6$alkoxy or $C_1$–$C_6$haloalkoxy; or $R_{31}$ is $C_5$–$C_7$cycloalkyl, $C_5$–$C_7$cycloalkenyl or $C_5$–$C_7$cycloakadienyl, which are unsubstituted or substituted by halogen, $C_1$–$C_4$alkyl, $C_1$–$C_4$alkoxy, $C_2$–$C_4$alkenyl, $C_2$–$C_4$alkynyl, $C_1$–$C_4$haloalkyl or $C_1$–$C_4$haloalkoxy; phenyl which is unsubstituted or substituted by halogen, $C_1$–$C_4$alkyl, $C_1$–$C_4$alkoxy, $C_1$–$C_4$haloalkyl or $C_1$–$C_4$haloalkoxy; thienyl, furyl, isoxazolyl, oxazolyl, thiadiazolyl, triazinyl, pyridyl, pyrimidinyl, pyrazinyl or pyridazinyl which are unsubstituted or substituted by halogen, $C_1$–$C_4$alkyl, $C_1$–$C_4$alkoxy, $C_1$–$C_4$haloalkyl or $C_1$–$C_4$haloalkoxy; or $R_{31}$ is cyclohexyl, cyclohexenyl or cyclohexadienyl, which are unsubstituted or substituted by halogen, $C_1$–$C_4$alkyl, $C_1$–$C_4$alkoxy, $C_1$–$C_4$haloalkyl or $C_1$–$C_4$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy; or $R_4$ is hydrogen; cyano; nitro; halogen; $C_1$–$C_4$alkoxy; $C_1$–$C_4$haloalkyl; $C_1$–$C_4$alkyl; $C_1$–$C_4$alkoxy-$C_1$–$C_4$alkyl; $C_5$–$C_7$cycloalkyl unsubstituted or substituted by $C_1$–$C_3$alkyl or $C_1$–$C_3$haloalkyl; $C_1$–$C_4$haloalkoxy-$C_1$–$C_4$alkyl: or $C_1$–$C_4$haloalkoxy; or R$_4$ is hydrogen; halogen; C$_1$–C$_4$alkoxy; C$_1$–C$_4$alkyl; C$_5$–C$_7$cycloalkyl unsubstituted or substituted by C$_1$–C$_3$alkyl or C$_1$–C$_3$haloalkyl; C$_1$–C$_4$haloalkyl; or C$_1$–C$_4$haloalkoxy; or R$_4$ is hydrogen; halogen; C$_1$–C$_3$alkoxy; C$_1$–C$_3$haloalkyl; C$_1$–C$_3$alkyl; C$_5$–C$_7$Cycloalkyl unsubstituted or substituted by C$_1$–C$_3$alkyl or C$_1$–C$_3$haloalkyl; or C$_1$–C$_3$haloalkoxy; or R$_5$, R$_6$, R$_7$, R$_8$ and R$_9$ are identical or different and are each independently of the others hydrogen, halogen, C$_1$–C$_4$haloalkyl, C$_1$–C$_4$alkyl, C$_1$–C$_6$haloalkoxy-C$_1$–C$_4$alkyl, C$_1$–C$_4$alkoxy, C$_1$–C$_4$haloalkoxy, C$_1$–C$_4$alkoxy-C$_1$–C$_4$alkyl or C$_3$–C$_7$cycloalkyl; or R$_5$, R$_6$, R$_7$ and R$_8$ are identical or different and are each independently of the others hydrogen, C$_1$–C$_4$haloalkyl, C$_1$–C$_4$alkyl, C$_1$–C$_4$alkoxy or C$_1$–C$_4$haloalkoxy; or R$_5$, R$_6$, R$_7$ and R$_8$ are identical or different and are each independently of the others hydrogen or C$_1$–C$_3$alkyl.

Within the group of compounds of formula I those compounds are preferred wherein:

R$_1$ is hydrogen, C$_1$–C$_4$alkyl, C$_1$–C$_4$haloalkyl, C$_1$–C$_4$alkoxy-C$_1$–C$_4$alkyl, C$_1$–C$_4$alkoxy, C$_1$–C$_4$haloalkoxy, C$_1$–C$_4$haloalkoxy-C$_1$–C$_4$alkyl or halogen;

R$_2$ is C$_1$–C$_4$alkyl, C$_1$–C$_4$haloalkyl, C$_1$–C$_4$alkoxy-C$_1$–C$_4$alkyl or C$_1$–C$_4$haloalkoxy-C$_1$–C$_4$alkyl;

A is a group

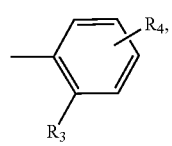 (A1)

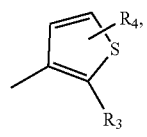 (A2)

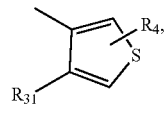 (A3)

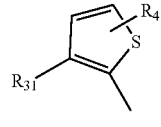 (A4)

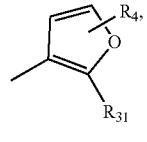 (A5)

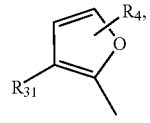 (A6)

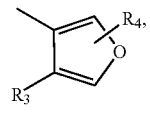 (A7)

-continued

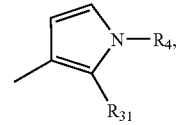 (A8)

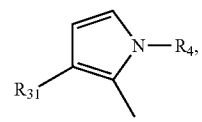 A(9)

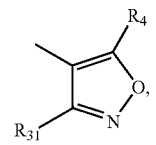 (A10)

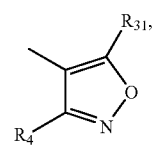 (A11)

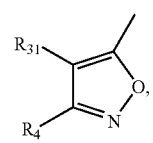 (A12)

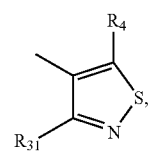 (A13)

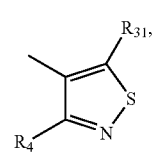 (A14)

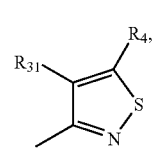 (A15)

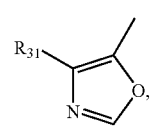 (A16)

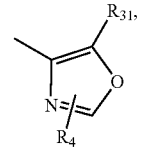 (A17)

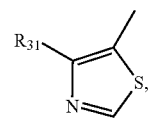 (A18)

-continued

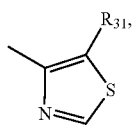
(A19)

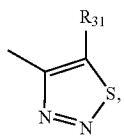
(A20)

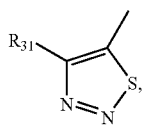
(A21)

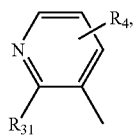
(A22)

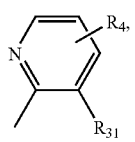
(A23)

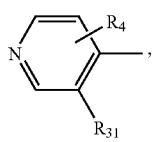
(A24)

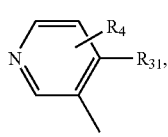
(A25)

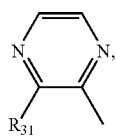
(A26)

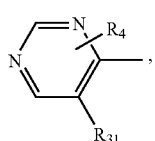
(A27)

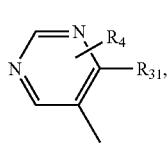
(A28)

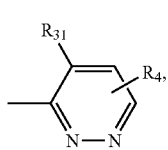
(A29)

-continued

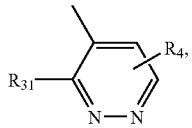
(A30)

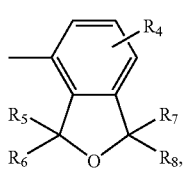
(A31)

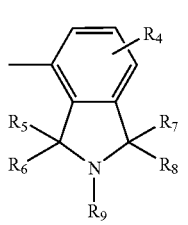
(A32)

and $R_3$ is $C_3$–$C_7$cycloalkyl unsubstituted or mono- to trisubstituted by halogen, hydroxy, $C_1$–$C_4$alkoxy, $C_1$–$C_4$haloalkyl, $C_2$–$C_4$alkenyl, $C_2$–$C_4$alkynyl, $C_1$–$C_4$haloalkoxy or $C_1$–$C_4$alkyl; $C_4$–$C_7$cycloalkenyl unsubstituted or mono- to trisubstituted by halogen, hydroxy, $C_1$–$C_4$alkoxy, $C_1$–$C_4$haloalkyl, $C_2$–$C_4$alkenyl, $C_2$–$C_4$alkynyl, $C_1$–$C_4$haloalkoxy or $C_1$–$C_4$alkyl; $C_6$–$C_7$cyclodialkenyl unsubstituted or mono- to trisubstituted by halogen, hydroxy, $C_1$–$C_4$alkoxy, $C_1$–$C_4$haloalkyl, $C_2$–$C_4$alkenyl, $C_2$–$C_4$alkynyl, $C_1$–$C_4$haloalkoxy or $C_1$–$C_4$alkyl; thienyl, furyl, pyrrolyl, pyrazolyl, oxazolyl, thiazolyl, isoxazolyl, isothiazolyl, thiadiazolyl, imidazolyl, tetrazolyl, triazinyl, benzothienyl, 5,6-dihydro-1,4,2-dioxazinyl, pyridyl, pyrazinyl, pyridazinyl or pyrimidinyl, which are unsubstituted or substituted by halogen, $C_1$–$C_6$haloalkyl, $C_1$–$C_6$alkyl, hydroxy, cyano, nitro, CHO, $C_1$–$C_4$alkoxy-$C_1$–$C_4$alkyl, COOC, —$C_4$alkyl, $C_1$–$C_6$haloalkoxy-$C_1$–$C_4$alkyl, $C_1$–$C_6$alkoxy or $C_1$–$C_6$haloalkoxy;

$R_{31}$ is $C_3$–$C_7$cycloalkyl, $C_3$–$C_7$cycloalkenyl or $C_5$–$C_7$cycloalkadienyl which are unsubstituted or substituted by halogen, $C_1$–$C_6$alkoxy, $C_1$–$C_6$alkoxy-$C_1$–$C_6$alkyl, $C_1$–$C_6$haloalkoxy-$C_1$–$C_4$alkyl, $C_1$–$C_4$alkyl, $C_1$–$C_4$haloalkyl, $C_1$–$C_4$haloalkoxy, $C_2$–$C_4$alkenyl or $C_2$–$C_5$alkynyl; phenyl unsubstituted or substituted by halogen, $C_1$–$C_6$alkoxy, $C_1$–$C_6$haloalkoxy, $C_1$–$C_4$alkyl, $C_1$–$C_4$haloalkyl, $C_2$–$C_4$alkenyl, $C_2$–$C_5$ alkynyl, CHO, COOC$_1$–$C_4$alkyl, $C_1$–$C_4$alkoxy-$C_1$–$C_4$alkyl, $C_1$–$C_4$alkyl-$C_1$–$C_4$alkoxy, $C_1$–$C_4$haloalkoxy-$C_1$–$C_4$alkyl, $C_1$–$C_4$haloalkyl-$C_1$–$C_4$alkoxy, cyano or nitro; thienyl, furyl, pyrrolyl, pyrazolyl, oxazolyl, thiazolyl, isoxazolyl, isothiazolyl, thiadiazolyl, imidazolyl, triazinyl, pyridyl, pyridazinyl, pyrazinyl or pyrimidinyl, which are unsubstituted or substituted by halogen, $C_1$–$C_6$haloalkyl, $C_1$–$C_6$alkyl, hydroxy, cyano, nitro, CHO, COOC$_1$–$C_4$alkyl, $C_1$–$C_6$haloalkoxy-$C_1$–$C_4$alkyl, $C_1$–$C_4$alkoxy-$C_1$–$C_4$alkyl, $C_1$–$C_6$alkoxy or $C_1$–$C_6$haloalkoxy;

$R_4$ is hydrogen; cyano; nitro; halogen; $C_1$–$C_4$alkoxy; $C_1$–$C_4$haloalkyl; $C_1$–$C_4$alkyl;

$C_1$–$C_4$alkoxy-$C_1$–$C_4$alkyl; $C_5$–$C_7$cycloalkyl unsubstituted or substituted by $C_1$–$C_3$alkyl or $C_1$–$C_3$haloalkyl; $C_1$–$C_4$haloalkoxy-$C_1$–$C_4$alkyl: or $C_1$–$C_4$haloalkoxy; and $R_5$, $R_6$, $R_7$, $R_8$ and $R_9$ are identical or different and are each independently of the others hydrogen, halogen, $C_1$–$C_4$haloalkyl, $C_1$–$C_4$alkyl, $C_1$–$C_6$haloalkoxy-$C_1$–$C_4$alkyl, $C_1$–$C_4$alkoxy, $C_1$–$C_4$haloalkoxy, $C_1$–$C_4$alkoxy-$C_1$–$C_4$alkyl or $C_3$–$C_7$cycloalkyl (subgroup AA).

Cycloalkyl is, depending on the ring size, cyclopropyl, cyclobutyl, cyclopentyl, cyclohexyl or cycloheptyl.

Cycloalkenyl is, depending on the ring size, cyclopentenyl, cyclohexenyl or cycloheptenyl.

Cycloalkadienyl is, depending on the ring size, cyclopentadienyl, cyclohexadienyl or cycloheptadienyl.

Alkenyl will be understood as meaning straight-chain or branched alkenyl such as allyl, methallyl, 1-methylvinyl or but-2-en1-yl. Preferred alkenyl radicals contain 3 to 4 carbon atoms in the chain.

Alkynyl can likewise, in accordance with the number of carbon atoms, be straight-chain or branched and is typically propargyl, but-1-yn-1-yl or but-1-yn-3yl.

Within the group AA of compounds of formula I those compounds are preferred wherein X is oxygen (subgroup AB).

Another group of compounds of formula I within the group AA are those wherein X is sulfur (subgroup AC).

Within the subgroup AB are those compounds preferred wherein $R_1$ is hydrogen, $C_1$–$C_4$alkyl or $C_1$–$C_4$haloalkyl;

$R_2$ is $C_1$–$C_4$alkyl, $C_1$–$C_3$haloalkyl or $C_1$–$C_3$alkoxy-$C_1$–$C_3$alkyl;

A is A1, A2, A3, A5, A8, A10, A13, A14, A17, A18, A20, A21, A22, A24, A25, A26, A27, A29, A31 or A32;

$R_3$ is $C_5$–$C_7$cycloalkyl, unsubstituted or mono- to trisubstituted by halogen, hydroxy, $C_2$–$C_4$alkenyl, $C_2$–$C_4$alkynyl, $C_1$–$C_3$alkyl or $C_1$–$C_3$alkoxy; $C_5$–$C_7$cycloalkenyl, unsubstituted or mono- to trisubstituted by halogen, hydroxy, $C_2$–$C_4$alkenyl, $C_2$–$C_4$alkynyl, $C_1$–$C_3$alkyl or $C_1$–$C_3$alkoxy; $C_6$–$C_7$cyclodialkenyl, unsubstituted or mono- to disubstituted by halogen, hydroxy, $C_2$–$C_4$alkenyl, $C_2$–$C_4$alkynyl, $C_1$–$C_3$alkyl or $C_1$–$C_3$alkoxy; thienyl, furyl, isoxazolyl, oxazolyl, thiadiazolyl, triazinyl, pyridyl, pyrimidinyl, pyrazinyl or pyridazinyl, which are unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy;

$R_{31}$ is $C_5$–$C_7$cycloalkyl, $C_5$–$C_7$cycloalkenyl or $C_5$–$C_7$Cycloakadienyl, which are unsubstituted or substituted by halogen, $C_1$–$C_4$alkyl, $C_1$–$C_4$alkoxy, $C_2$–$C_4$alkenyl, $C_2$–$C_4$alkynyl, $C_1$–$C_4$haloalkyl or $C_1$–$C_4$haloalkoxy; phenyl which is unsubstituted or substituted by halogen, $C_1$–$C_4$alkyl, $C_1$–$C_4$alkoxy, $C_1$–$C_4$haloalkyl or $C_1$–$C_4$haloalkoxy; thienyl, furyl, isoxazolyl, oxazolyl, thiadiazolyl, triazinyl, pyridyl, pyrimidinyl, pyrazinyl or pyridazinyl which are unsubstituted or substituted by halogen, $C_1$–$C_4$alkyl, $C_1$–$C_4$alkoxy, $C_1$–$C_4$haloalkyl or $C_1$–$C_4$haloalkoxy;

$R_4$ is hydrogen; halogen; $C_1$–$C_4$alkyl; $C_1$–$C_4$alkoxy; $C_5$–$C_7$cycloalkyl unsubstituted or substituted by $C_1$–$C_3$alkyl or $C_1$–$C_3$haloalkyl; $C_1$–$C_4$haloalkyl; or $C_1$–$C_4$haloalkoxy; and $R_5$, $R_6$, $R_7$ and $R_8$ are identical or different and are each independently of the others hydrogen, $C_1$–$C_4$alkyl, $C_1$–$C_4$alkoxy, $C_1$–$C_4$haloalkyl or $C_1$–$C_4$haloalkoxy (subgroup AB1).

Within the subgroup AB1 are those compounds more preferred wherein

A is A1, A2, A3, A17, A20, A21, A24, A25, A26, A27 or A31;

$R_1$ is hydrogen or $C_1$–$C_3$alkyl;

$R_2$ is $C_1$–$C_3$alkyl or $C_1$–$C_3$alkoxy-$C_1$–$C_3$alkyl;

$R_3$ is cyclohexyl, cyclohexenyl or cyclohexadienyl, which are unsubstituted or mono- to disubstituted by chloro, bromo, $C_1$–$C_2$alkyl, $C_1$–$C_2$haloalkyl or $C_1$–$C_2$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy;

$R_{31}$ is cyclohexyl, cyclohexenyl or cyclohexadienyl, which are unsubstituted or substituted by halogen, $C_1$–$C_4$alkyl, $C_1$–$C_4$alkoxy, $C_1$–$C_4$haloalkyl or $C_1$–$C_4$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy;

$R_4$ is hydrogen; halogen; $C_1$–$C_3$alkyl; $C_1$–$C_3$haloalkyl; $C_1$–$C_3$alkoxy; $C_5$–$C_7$cycloalkyl unsubstituted or substituted by $C_1$–$C_3$alkyl or $C_1$–$C_3$haloalkyl; or $C_1$–$C_3$haloalkoxy; and $R_5$, $R_6$, $R_7$ and $R_8$ are identical or different and are each independently of the others hydrogen or $C_1$–$C_3$alkyl (subgroup AB2).

Within the subgroup AC are those compounds preferred wherein $R_1$ is hydrogen, $C_1$–$C_4$alkyl or $C_1$–$C_4$haloalkyl;

$R_2$ is $C_1$–$C_4$alkyl, $C_1$–$C_3$haloalkyl or $C_1$–$C_3$alkoxy-$C_1$–$C_3$alkyl;

A is A1, A2, A3, A5, A8, A10, A13, A14, A17, A18, A20, A21, A22, A24, A25, A26, A27, A29, A31 or A32;

$R_3$ is $C_5$–$C_7$cycloalkyl, unsubstituted or mono- to trisubstituted by halogon, hydroxy, $C_2$–$C_4$alkenyl, $C_2$–$C_4$alkynyl, $C_1$–$C_3$alkyl or $C_1$–$C_3$alkoxy; $C_5$–$C_7$cycloalkenyl, unsubstituted or mono- to trisubstituted by halogen, hydroxy, $C_2$–$C_4$alkenyl, $C_2$–$C_4$alkynyl, $C_1$–$C_3$alkyl or $C_1$–$C_3$alkoxy; $C_6$–$C_7$cyclodialkenyl, unsubstituted or mono- to disubstituted by halogen, hydroxy, $C_2$–$C_4$alkenyl, $C_2$–$C_4$alkynyl, $C_1$–$C_3$alkyl or $C_1$–$C_3$alkoxy; thienyl, furyl, isoxazolyl, oxazolyl, thiadiazolyl, triazinyl, pyridyl, pyrimidinyl, pyrazinyl or pyridazinyl, which are unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy;

$R_{31}$ is $C_5$–$C_7$cycloalkyl, $C_5$–$C_7$cycloalkenyl or $C_5$–$C_7$cycloakadienyl, which are unsubstituted or substituted by halogen, $C_1$–$C_4$alkyl, $C_1$–$C_4$alkoxy, $C_2$–$C_4$alkenyl, $C_2$–$C_4$alkynyl, $C_1$–$C_4$haloalkyl or $C_1$–$C_4$haloalkoxy; phenyl which is unsubstituted or substituted by halogen, $C_1$–$C_4$alkyl, $C_1$–$C_4$alkoxy, $C_1$–$C_4$haloalkyl or $C_1$–$C_4$haloalkoxy; thienyl, furyl, isoxazolyl, oxazolyl, thiadiazolyl, triazinyl, pyridyl, pyrimidinyl, pyrazinyl or pyridazinyl which are unsubstituted or substituted by halogen, $C_1$–$C_4$alkyl, $C_1$–$C_4$alkoxy, $C_1$–$C_4$haloalkyl or $C_1$–$C_4$haloalkoxy;

$R_4$ is hydrogen; halogen; $C_1$–$C_4$alkyl; $C_1$–$C_4$alkoxy; $C_1$–$C_4$haloalkyl; $C_5$–$C_7$cycloalkyl unsubstituted or substituted by $C_1$–$C_3$alkyl or $C_1$–$C_3$haloalkyl; or $C_1$–$C_4$haloalkoxy; and $R_5$, $R_6$, $R_7$ and $R_8$ are identical or different and are each independently of the others hydrogen, $C_1$–$C_4$alkyl, $C_1$–$C_4$alkoxy, $C_1$–$C_4$haloalkyl or $C_1$–$C_4$haloalkoxy (subgroup AC1).

Within the subgroup AC1 are those compounds more preferred wherein

A is A1, A2, A3, A17, A20, A21, A24, A25, A26, A27 or A31;

$R_1$ is hydrogen or $C_1$–$C_3$alkyl;

$R_2$ is $C_1$–$C_3$alkyl or $C_1$–$C_3$alkoxy-$C_1$–$C_3$alkyl;

$R_3$ is cyclohexyl, cyclohexenyl or cyclohexadienyl, which are unsubstituted or mono- to disubstituted by chloro, bromo, $C_1$–$C_2$alkyl, $C_1$–$C_2$haloalkyl or $C_1$–$C_2$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy;

$R_{31}$ is cyclohexyl, cyclohexenyl or cyclohexadienyl, which are unsubstituted or substituted by halogen, $C_1$–$C_4$alkyl, $C_1$–$C_4$alkoxy, $C_1$–$C_4$haloalkyl or $C_1$–$C_4$haloalkoxy; thienyl, furyl, triazinyl, pyridyl, pyrazinyl, pyridazinyl or pyrimidinyl which are unsubstituted or substituted by halogen, $C_1$–$C_4$alkyl, $C_1$–$C_4$haloalkyl or $C_1$–$C_4$haloalkoxy;

$R_4$ is hydrogen; halogen; $C_1$–$C_3$alkyl; $C_1$–$C_3$haloalkyl; $C_1$–$C_3$alkoxy; $C_5$–$C_7$cycloalkyl unsubstituted or substituted by $C_1$–$C_3$alkyl or $C_1$–$C_3$haloalkyl; or $C_1$–$C_3$haloalkoxy; and $R_5$, $R_6$, $R_7$ and $R_8$ are identical or different and are each independently of the others hydrogen or $C_1$–$C_3$alkyl (subgroup AC2).

Whithin the subgroup AB are those compounds preferred wherein

A is A1 and $R_3$ is $C_5$–$C_7$cycloalkyl unsubstituted or monosubstituted by $C_1$–$C_4$alkyl or $C_1$–$C_4$haloalkyl (subgroup AB3).

Preferred individual compounds are:

1-methyl-4-trifluoromethyl-1H-pyrrole-3-carboxylic acid [1'-(3'-methylcyclohexyl)-2-benzamide];

1-methyl-4-trifluoromethyl-1H-pyrrole-3-carboxylic acid [1'-(3'-ethylcyclohexyl)-2-benzamide];

1-methyl-4-trifluoromethyl-1H-pyrrole-3-carboxylic acid [1'-(3'-trifluoromethylcyclohexyl)-2-benzamide];

1-methyl-4-trifluoromethyl-1H-pyrrole-3-carboxylic acid [1'-(3'-methylcyclopentyl)-2-benzamide];

1-methyl-4-trifluoromethyl-1H-pyrrole-3-carboxylic acid [1'-(3'-ethylcyclopentyl)-2-benzamide];

1-methyl-4-trifluoromethyl-1H-pyrrole-3-carboxylic acid [1'-(3'-trifluoromethylcyclopentyl)-2-benzamide].

The compounds according to formula I may be prepared according to the following reaction schemes.

A) Synthesis of the Pyrrole Carboxylic Acids:

Route 1 (Tosmic-Route)

Scheme 1

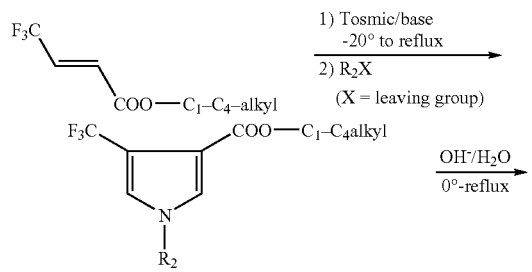

-continued

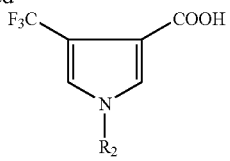

Route 2 (Trifluoroacetoacetic Acid-Route, Analogous to JP-07157466)

Scheme 2

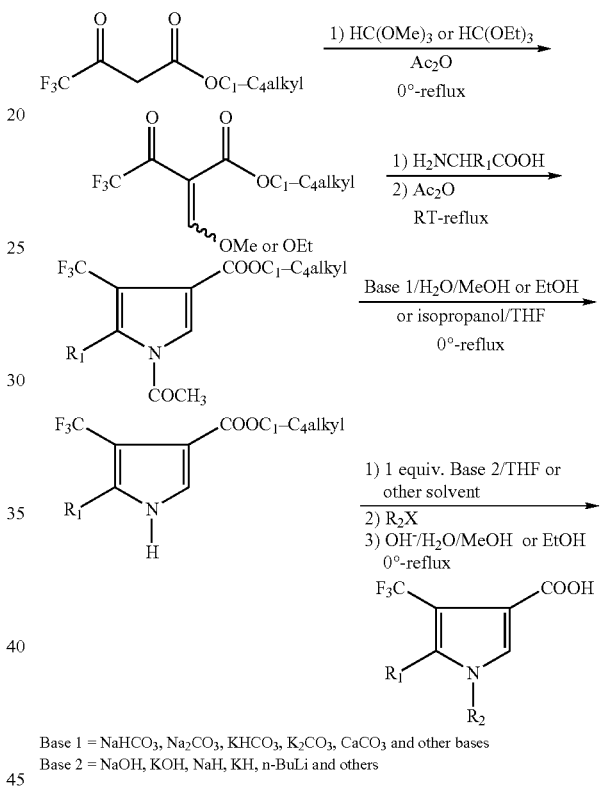

Base 1 = NaHCO$_3$, Na$_2$CO$_3$, KHCO$_3$, K$_2$CO$_3$, CaCO$_3$ and other bases
Base 2 = NaOH, KOH, NaH, KH, n-BuLi and others B) Synthesis of the Amides/Thioamides Scheme 3

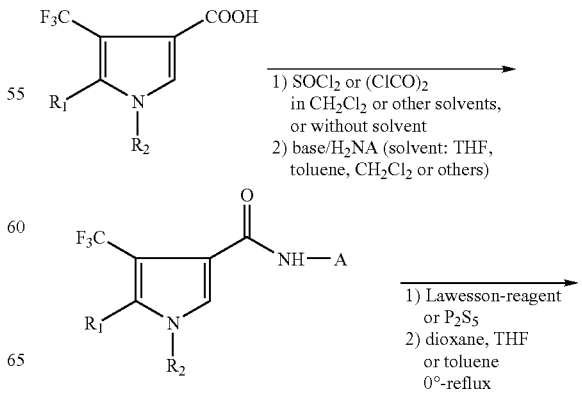

-continued

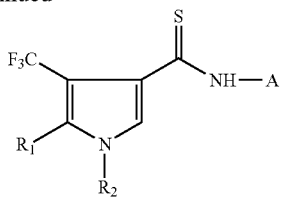

Base = NEt₃, Hünig-base, Na₂CO₃, K₂CO₃ and others

B1) Synthesis of the Amides Wherein A is Phenyl, Pyridine or Pyrimidine

Scheme 4

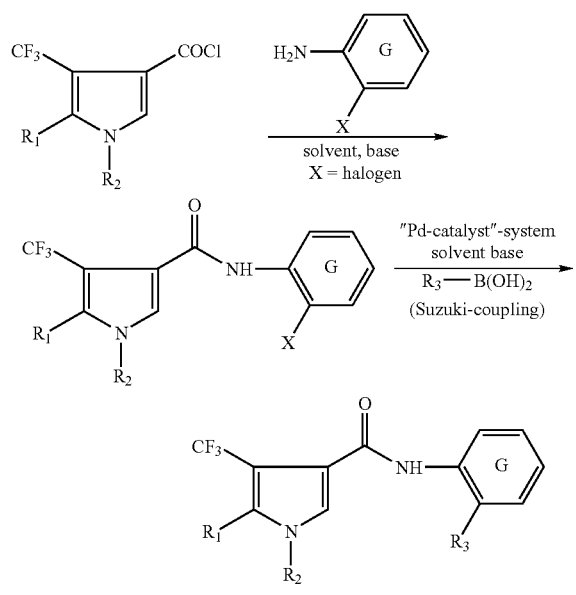

G = phenyl, pyridine, pyrimidine

The "in situ" prepared pyrazole carboxylic acid chloride reacts with an ortho-halosubstituted phenylamine in the presence of a solvent like toluene, benzene, xylene, hexane, cyclohexane, THF, chloroform or methylenechloride and in the presence of a base like sodium carbonate, sodium hydrogencarbonate, potassium carbonate, Hünig base, triethylamine or pyridine at a temperature between 0° C. and reflux temperature. The obtained pyrazolecarboxamide reacts with a boronic acid of the formula $R_3$-B(OH)$_2$ in the presence of a Pd-catalyst like Pd(P(phenyl)$_3$)$_4$, Pd(P(phenyl)$_3$))$_2$Cl$_2$, PdCl$_2$dppb, Pd$_2$(dba)$_3$, Pd(OAc)$_2$, PdOAc$_2$/(o-tolyl)$_3$P, Pd(OAc)$_2$/dppf, Pd(PhCN)$_2$Cl$_2$/Ph$_3$As, Pd(CH$_3$CN)$_2$Cl$_2$, Pd$_2$(dba)$_3$/P(tert.butyl)$_3$, Pd(OAc)$_2$/P(tert.butyl)$_2$biphenyl, Pd(OAc)$_2$/TPPTS, Pd(OAc)$_2$/PCy$_3$, Pd(OAc)$_2$/P(O-i-Pr)$_3$, Pd(OAc)$_2$/2-dimethylamino-2'-dicyclohexylphosphinobiphenyl, Pd(OAc)$_2$/2-dimethylamino-2'-ditert.butylphosphinobiphenyl, Pd(OAc)$_2$/(o-biphenyl)P(cyclohexyl)$_2$ in a solvent like 1,2-dimethoxyethane/water, DMF, DMA, THF/water, dioxane/water, benzene, toluene, xylene and others and a base like sodium carbonate, sodium hydrogencarbonate, potassium carbonate, cesium carbonate, potassium phosphate, triethylamine, sodium hydroxide, sodium ethylate, sodium tert.butylate, silver oxide, barium carbonate, potassium fluoride or cesium fluoride at a temperature between 0° C. and reflux temperature.

C) Synthesis of the Ortho-Substituted Amines A-NH$_2$:

The compounds are either known from the literature or can be prepared by known methods. For example the following amines or important intermediates for the synthesis of the amines can be prepared according to the following literature:

$A_1$-NH$_2$: Tetrahedron 1993, 49, 49–64 or EP-83975 or J.Org.Chem. 1995, 60, 292;
$A_2$-NH$_2$: EP-737682;
$A_3$-NH$_2$: J.Chem.Res.(S) 1978, 11, 428 or Chem.Scr. 1972, 2, 245;
$A_{17}$-NH$_2$: Org.Prep.Procedures Int. 1989, 21, 141;
$A_{21}$-NH$_2$: J.Chem.Soc.Perkin I 1981, 5, 1591;
$A_{25}$-NH$_2$: Tetrahedron 1993, 49, 49–64 or Heterocycles 1999, 51, 721;
$A_{26}$-NH$_2$: Synthesis 1996, 10, 1015 or Synthesis 1994, 9, 931;
$A_{27}$-NH$_2$: Liebigs Ann.Chemie 1977, 537–544 or J.Med. Chem. 1975, 18, 623;
$A_{31}$-NH$_2$: EP-315502;
$A_{32}$-NH$_2$: J.Pesticide Science 1993, 18, 245;
$A_{30}$-NH$_2$: J.Heterocyclic Chem. 1982, 19, 1285.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, Erwinia amylovora as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilisers, antifoams, viscosity regulators, binders or tackifiers as well as fertilisers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilisers. Such carriers are for example described in WO 97/33890.

The compounds of formula I are normally used in the form of compositions and can be applied to the crop area or plant to be treated, simultaneously or in succession with further compounds. These further compounds can be e.g. fertilisers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2, 4-dichlorophenoxy)-propionamide (AC 382042), or iprovalicarb (SZX 722).

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting examples illustrate the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

EXAMPLE 1

1-Methyl-4-trifluoromethyl-1H-pyrrole-3-carboxylic acid [4-(4'-chlorophenyl)pyridin-3-yl]amide a) 1-Methyl-4-trifluoromethylpyrrole-3-carboxylic acid

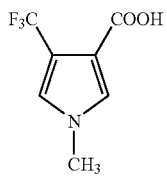

Sodium hydride (8.0 g of a 75% dispersion in oil) is suspended at +5° C. in a mixture of DMSO (300 ml) and diethylether (100 ml). A solution of ethyl 4,4,4-trifluorocrotonate (20 g) and TOSMIC (23 g) in DMSO (100 ml) is added through a dropping funnel at such a rate that the temperature does not exceed 10° C. After stirring the reaction mixture for an additional hour at room temperature methyl iodide (15.6 ml) is added with cooling. After 2 hours at room temperature the reaction mixture is poured onto crushed ice. Repeated extraction with ether, washing of the combined organic phases with brine and evaporation of the solvent under reduced pressure gives a product mixture in form of a light amber oil. The crude product mixture is heated at 60° C. in a mixture of ethanol (100 ml) and sodium hydroxide (50 ml of a 30% aqueous solution). Washing of the solution with ether, acidifying of the aqueous phase with concentrated hydrochloric acid and filtering gives the 1-methyl-4-trifluoromethylpyrrole-3-carboxylic acid in form of a crystalline solid. $^1$H-NMR (CDCl$_3$): 7.24(d,1H); 6.88(d, 1H); 3.63(s,3H).

In analogous manner the new compounds 1-ethyl- (m.p.146–148° C.) and 1-methoxymethyl-4-trifluoromethylpyrrole-3-carboxylic acid can be prepared.

b) 4-(4'-chlorophenyl)-3-nitropyridine

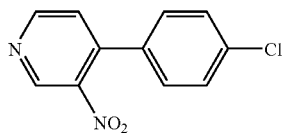

In a sulfonation flask 6.9 g (44 mmol) of 4-chloro-3-nitropyridine, 6.5 g (42 mmol) 4-chloro-phenylboronic acid, 6.0 g (44 mmol) potassium carbonate (saturated solution in water) and 1.0 g (0.9 mmol) tetrakis(triphenylphosphine) palladium are dissolved in 100 ml of dimethoxyethane (DME). The mixture is heated under reflux conditions under a constant nitrogen stream for 5 hours. Then the solvent is removed in a water jet vacuum and the residue taken up in ethylacetate. The organic phase is washed twice with water and after drying of the organic phase with sodium sulfate, the solvent is removed in a water jet vacuum. The resulting crude product is purified by column chromatography over silica gel (eluant: hexane/ethylacetate 1:1). Yield: 8.9 g 4-(4'-chlorophenyl)-3-nitropyridine in the form of brownish crystals; m.p. 74–76° C.

c) 3-amino-4-(4'-chlorophenyl)pyridine

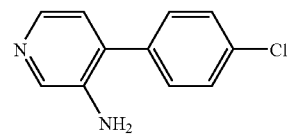

In a sulfonation flask 8.4 g (36 mmol) 4-(4'-chlorophenyl)-3-nitropyridine is dissolved in a mixture of 100 ml water, 35 ml acetic acid and 10 ml n-propanol. After the addition of 7.0 g (125 mmol) iron powder, the mixture is heated for 3 hours under reflux conditions. After cooling to room temperature the mixture is diluted with ethylacetate and filtered over hyflo. Then the filtrate is neutralized by the addition of sodiumbicarbonate solution and the organic phase separated. The water phase is extracted twice with ethylacetate and the combined organic phases dried over sodium sulfate. After distilling off the solvent in a water jet vacuum the obtained raw material is purified by column chromatography over silica gel (eluant: ethylacetate). Yield: 3.9 g 3-amino-4-(4'-chlorophenyl)pyridine in the form of a slightly brownish powder; m.p.: 144–146° C.

d) 1-Methyl-4-trifluoromethyl-1H-pyrrole-3-carboxylic acid [4-(4'-chlorophenyl)-pyridin-3-yl]amide

[cmpd. 6.10]

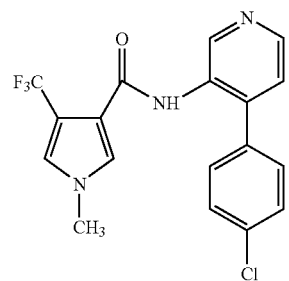

A solution of 0.54 g (2.8 mmol) 1-methyl-4-trifluoromethylpyrrole-3-carboxylic acid and 0.39 g (3.1 mmol) oxalyl chloride in 20 ml methylene chloride is stirred for 2 hours at room temperature in the presence of a catalytic amount of DMF. Then the acid chloride solution is slowly added to a solution of 0.57 g (2.8 mmol) 3-amino-4-(4'-chlorophenyl) pyridine, 0.34 g (3.4 mmol) triethylamine and 15 ml methylene chloride. The resulting mixture is then stirred for 16 hours at room temperature. After the addition of ethylacetate, the organic phase is washed twice with water. After drying the organic phase over sodium sulfate, the solvent is removed in a water jet vacuum. The obtained crude product is purified by column chromatography over silica gel (eluant: hexane/THF 1:3). Yield: 0.4 g 1-methyl-4-trifluoromethyl-1H-pyrrole-3-carboxylic acid [4-(4'-chlorophenyl)-pyridin-3-yl]amide in the form of yellowish crystals; m.p.: 178–180° C.

EXAMPLE 2

1-Methyl-4-trifluoromethyl-1H-pyrrole-3-carboxylic acid (2-bromo-benzamide)

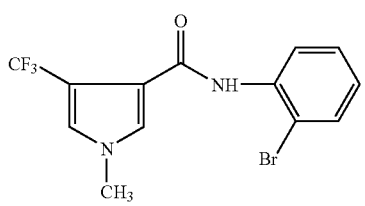

A solution of 7.8 g (40.4 mmol) 1-methyl-4-trifluoromethylpyrrole-3-carboxylic acid and 3.8 ml (45 mmol) oxalyl chloride in 100 ml dichloromethane is stirred for 1 hour at room temperature in the presence of a catalytic amount of DMF. Then the resulting acid chloride solution is slowly added to a solution of 6.95 g (40.4 mmol) 2-bromoaniline, 6.9 ml (49 mmol) triethylamine and 140 ml dichloromethane. The resulting mixture is then stirred for 16 hours at room temperature. The organic phase is washed twice with water and dried over sodium sulfate. The solvent is removed under reduced pressure. The crude product is purified by column chromatography over silica gel (eluant: ethylacetate/hexane=2/3); yield: 11.4 g 1-methyl-4-trifluoromethyl-1H-pyrrole-3-carboxylic acid (2-bromo-benzamide) as colourless crystals; m.p. 117–119° C.

EXAMPLE 3

1-Methyl-4-trifluoromethyl-1H-pyrrole-3-carboxylic acid [2'-(5'-chloro-thienyl)-2-benzamide]

[cmpd. 1.20]

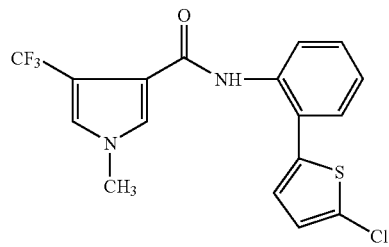

To 1.0 g (2.9 mmol) 1-methyl-4-trifluoromethyl-1H-pyrrole-3-carboxylic acid (2-bromo-benzamide), 0.56 g (3.5 mmol) 5-chloro-thiophene-2-boronic acid and 0.12 g (0.2 mmol) bis(triphenylphosphine)palladium(II) chloride in 20 ml ethylene glycol dimethyl ether is added a solution of 0.87 g (10.4 mmol) sodium hydrogencarbonate in 20 ml water. The reaction mixture is then stirred for 24 hours at 70° C. After the addition of dichloromethane, the organic phase is washed twice with water and with sodium chloride solution. After drying over sodium sulfate, the solvent is removed under reduced pressure. The product is purified by column chromatography over silica gel (eluant: dichloromethane/hexane=4/1) to obtain 1-methyl-4-trifluoromethyl-1H-pyrrole-3-carboxylic acid [2'-(5'-chloro-thienyl)-2-benzamide] as colourless crystals; m.p. 139–141° C.

The following compounds are prepared in a similar way, using analogous methods.

TABLE 1

Compounds of the formula I, wherein A = A1 =

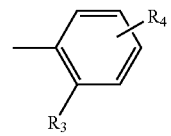

| Compd. No. | $R_1$ | $R_2$ | X | $R_3$ | $R_4$ | Phys. Data [m.p. ° C.] |
|---|---|---|---|---|---|---|
| 1.1 | H | $CH_3$ | O | HO-cyclohexyl | H | |
| 1.2 | H | $CH_3$ | O | Cl-cyclohexyl | H | |
| 1.3 | H | $CH_3$ | O | Cl,Cl-cyclohexyl | H | |

TABLE 1-continued

Compounds of the formula I, wherein A = A1 =

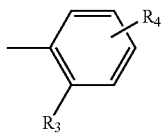

| Compd. No. | $R_1$ | $R_2$ | X | $R_3$ | $R_4$ | Phys. Data [m.p. ° C.] |
|---|---|---|---|---|---|---|
| 1.4 | H | $CH_3$ | O | 1,2-dibromo-1-methylcyclohexyl | H | |
| 1.5 | H | $CH_3$ | O | 6-chlorocyclohex-1-enyl | H | |
| 1.6 | H | $CH_3$ | O | 6-bromocyclohex-1-enyl | H | |
| 1.7 | H | $CH_3$ | O | cyclohexa-1,3-dienyl | H | |
| 1.8 | H | $CH_3$ | O | 4-chlorocyclohex-1-enyl | H | |
| 1.9 | H | $CH_3$ | O | 4-bromocyclohex-1-enyl | H | |
| 1.10 | H | $CH_3$ | O | 4,4-dichlorocyclohex-1-enyl | H | |
| 1.11 | H | $CH_3$ | O | 4-methylcyclohexyl | H | 127–129 |
| 1.12 | H | $CH_2CH_3$ | O | 4-methylcyclohexyl | H | |
| 1.13 | H | $CH_3$ | S | 4-methylcyclohexyl | H | |
| 1.14 | H | $CH_3$ | O | 4,4-dimethylcyclohexyl | H | |
| 1.15 | H | $CH_3$ | O | 4-ethylcyclohexyl | H | 131–132 |

TABLE 1-continued

Compounds of the formula I, wherein A = A1 =

[structure: benzene ring with R4 and R3 substituents]

| Compd. No. | R₁ | R₂ | X | R₃ | R₄ | Phys. Data [m.p. ° C.] |
|---|---|---|---|---|---|---|
| 1.16 | H | CH₃ | S | cyclohexyl-CH₂CH₃ | H | resin |
| 1.17 | CH₃ | CH₃ | O | Cl-cyclohexyl-CH₃ | H | |
| 1.18 | H | CH₂OCH₃ | O | cyclohexyl-CH₃ | H | |
| 1.19 | H | CH₃ | O | methylthiophene | H | 116–118 |
| 1.20 | H | CH₃ | O | methyl-Cl-thiophene | H | 139–141 |
| 1.21 | H | CH₃ | O | methylthiophene | H | 132–136 |
| 1.22 | H | CH₃ | O | Cl-methylthiophene | H | |
| 1.23 | H | CH₃ | O | methylfuran | H | 106–109 |
| 1.24 | H | CH₃ | O | methylisoxazole | H | 182–185 |
| 1.25 | H | CH₂OCH₃ | O | methylisoxazole | H | 171–173 |
| 1.26 | H | CH₃ | O | methylisoxazole | H | 132–134 |
| 1.27 | H | CH₂OCH₃ | O | methylisoxazole | H | |
| 1.28 | H | CH₃ | O | Cl-dimethylisoxazole | H | |

TABLE 1-continued

Compounds of the formula I, wherein A = A1 =

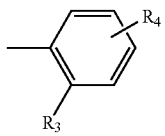

| Compd. No. | R$_1$ | R$_2$ | X | R$_3$ | R$_4$ | Phys. Data [m.p. ° C.] |
|---|---|---|---|---|---|---|
| 1.29 | H | CH$_3$ | O | 5-methyl-oxazol-2-yl | H | |
| 1.30 | H | CH$_3$ | O | 4-methyl-oxazol-2-yl | H | |
| 1.31 | H | CH$_3$ | O | 5-chloro-4-methyl-1,2,3-thiadiazole | H | |
| 1.32 | H | CH$_3$ | O | pyridin-4-yl | H | |
| 1.33 | H | CH$_3$ | O | 2-chloropyridin-4-yl | H | |
| 1.34 | H | CH$_2$CH$_3$ | O | 2-chloropyridin-4-yl | H | |
| 1.35 | H | CH$_2$OCH$_3$ | O | 2-chloropyridin-4-yl | H | |
| 1.36 | H | CH$_3$ | O | 2-fluoropyridin-4-yl | H | |
| 1.37 | H | CH$_3$ | O | 2-hydroxypyridin-4-yl | H | |
| 1.38 | H | CH$_3$ | O | 2-trifluoromethoxypyridin-4-yl | H | |

TABLE 1-continued

Compounds of the formula I, wherein A = A1 =

| Compd. No. | $R_1$ | $R_2$ | X | $R_3$ | $R_4$ | Phys. Data [m.p. ° C.] |
|---|---|---|---|---|---|---|
| 1.39 | H | $CH_3$ | O | 3-Cl-pyridin-4-yl | H | |
| 1.40 | H | $CH_3$ | O | 3-F-pyridin-4-yl | H | 169–171 |
| 1.41 | H | $CH_2OCH_3$ | O | 3-F-pyridin-4-yl | H | |
| 1.42 | H | $CH_3$ | O | pyridin-3-yl | H | 143–145 |
| 1.43 | H | $CH_3$ | S | pyridin-3-yl | H | |
| 1.44 | H | $CH_3$ | O | 2-Cl-pyridin-3-yl | H | |
| 1.45 | H | $CH_3$ | O | 2-F-pyridin-3-yl | H | |
| 1.46 | H | $CH_2OCH_3$ | O | 2-F-pyridin-3-yl | H | |
| 1.47 | H | $CH_3$ | O | 2-$CF_3$-pyridin-3-yl | H | |
| 1.48 | H | $CH_3$ | O | 2-$OCF_3$-pyridin-3-yl | H | |

TABLE 1-continued
Compounds of the formula I, wherein A = A1 =
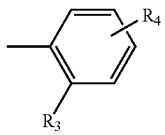
| Compd. No. | R₁ | R₂ | X | R₃ | R₄ | Phys. Data [m.p. ° C.] |
|---|---|---|---|---|---|---|
| 1.49 | H | CH₃ | O | 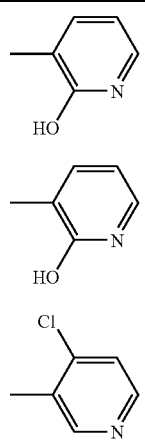 | H | >230 |
| 1.50 | H | CH₂OCH₃ | O | | H | >230 |
| 1.51 | H | CH₃ | O | 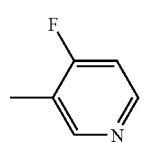 | H | |
| 1.52 | H | CH₃ | O | 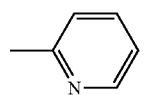 | H | |
| 1.53 | H | CH₃ | O | 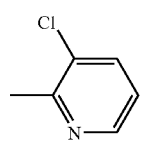 | H | |
| 1.54 | H | CH₃ | O | 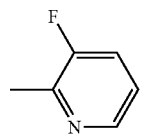 | H | |
| 1.55 | H | CH₃ | O | | H | |
| 1.56 | H | CH₃ | O | 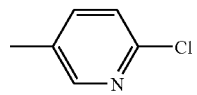 | H | |
| 1.57 | H | CH₃ | O | 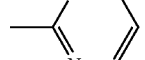 | H | |
| 1.58 | H | CH₃ | O | 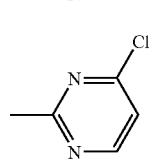 | H | |

TABLE 1-continued
Compounds of the formula I, wherein A = A1 =
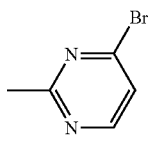
| Compd. No. | R₁ | R₂ | X | R₃ | R₄ | Phys. Data [m.p. ° C.] |
|---|---|---|---|---|---|---|
| 1.59 | H | CH₂CH₃ | O | 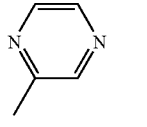 | H | |
| 1.60 | H | CH₃ | O | 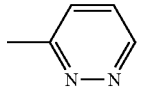 | H | |
| 1.61 | H | CH₃ | O | 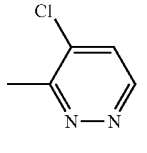 | H | |
| 1.62 | H | CH₃ | O | 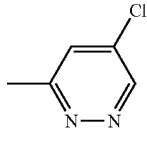 | H | |
| 1.63 | H | CH₃ | O | 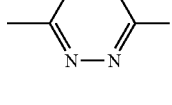 | H | |
| 1.64 | H | CH₃ | O | 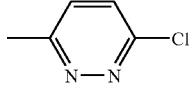 | H | |
| 1.65 | CH₃ | CH₃ | O | 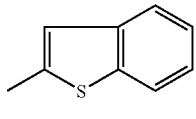 | H | |
| 1.66 | H | CH₃ | O | 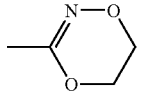 | H | 126–128 |
| 1.67 | H | CH₃ | O | 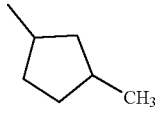 | H | 164–165 |
| 1.68 | H | CH₃ | O |  | H | 118–119 |

TABLE 1-continued
Compounds of the formula I, wherein A = A1 =
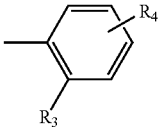
| Compd. No. | $R_1$ | $R_2$ | X | $R_3$ | $R_4$ | Phys. Data [m.p. ° C.] |
|---|---|---|---|---|---|---|
| 1.69 | H | $CH_2OCH_3$ | O | 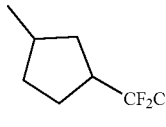 | H | oil; $^1$H-NMR, MS |
| 1.70 | H | $CH_3$ | O | 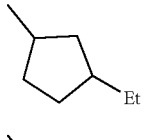 | H | |
| 1.71 | H | $CH_2OCH_3$ | O | 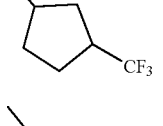 | H | |
| 1.72 | H | $CH_3$ | O | 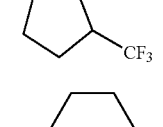 | H | |
| 1.73 | H | $CH_2OCH_3$ | O | 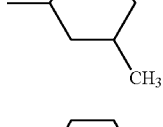 | H | |
| 1.74 | H | $CH_3$ | O | 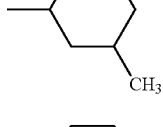 | H | 93–95 |
| 1.75 | H | $CH_2OCH_3$ | O | 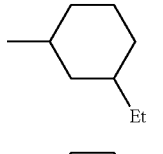 | H | oil; $^1$H-NMR, MS |
| 1.76 | H | $CH_3$ | O | 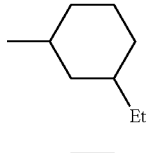 | H | |
| 1.77 | H | $CH_2OCH_3$ | O | | H | |
| 1.78 | H | $CH_3$ | O | 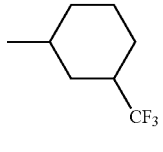 | H | |

TABLE 1-continued
Compounds of the formula I, wherein A = A1 =
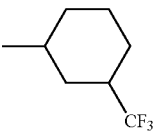
| Compd. No. | $R_1$ | $R_2$ | X | $R_3$ | $R_4$ | Phys. Data [m.p. ° C.] |
|---|---|---|---|---|---|---|
| 1.79 | H | CH$_2$OCH$_3$ | O | 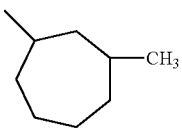 | H | |
| 1.80 | H | CH$_3$ | O | 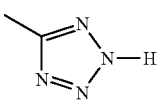 | H | |
| 1.81 | H | CH$_3$ | O | 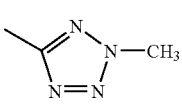 | H | 250–252 |
| 1.82 | H | CH$_3$ | O |  | H | 202–204 |
TABLE 2
Compounds of the formula I, wherein A = A2 =
| Compd. No. | $R_1$ | $R_2$ | X | $R_3$ | $R_4$ | Phys. Data [m.p. ° C.] |
|---|---|---|---|---|---|---|
| 2.1 | H | CH$_3$ | O | 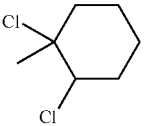 | H | |
| 2.2 | H | CH$_3$ | O | 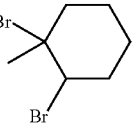 | H | |
| 2.3 | H | CH$_3$ | O | | H | |
| 2.4 | H | CH$_3$ | O | | H | |

TABLE 2-continued
Compounds of the formula I, wherein A = A2 =
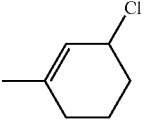
| Compd. No. | R$_1$ | R$_2$ | X | R$_3$ | R$_4$ | Phys. Data [m.p. ° C.] |
|---|---|---|---|---|---|---|
| 2.5 | H | CH$_3$ | O | 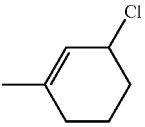 | H | |
| 2.6 | H | CH$_2$OCH$_3$ | O | 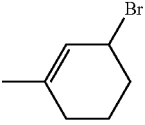 | H | |
| 2.7 | H | CH$_3$ | O | 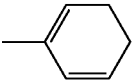 | H | |
| 2.8 | H | CH$_3$ | O | 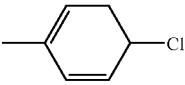 | H | |
| 2.9 | H | CH$_3$ | O |  | H | |
| 2.10 | H | CH$_3$ | O |  | H | |
| 2.11 | H | CH$_3$ | O | 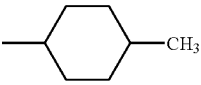 | H | |
| 2.12 | H | CH$_3$ | O | 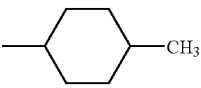 | H | resin |
| 2.13 | H | CH$_3$ | S | 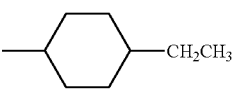 | H | |
| 2.14 | H | CH$_3$ | O | 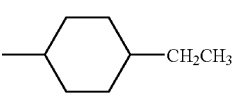 | H | |
| 2.15 | H | CH$_3$ | S | 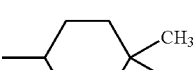 | H | |
| 2.16 | H | CH$_3$ | O |  | H | |

TABLE 2-continued
Compounds of the formula I, wherein A = A2 =
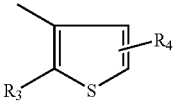
| Compd. No. | R₁ | R₂ | X | R₃ | R₄ | Phys. Data [m.p. ° C.] |
|---|---|---|---|---|---|---|
| 2.17 | CH₃ | CH₃ | O | 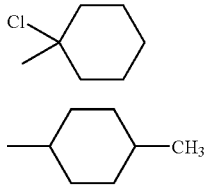 | H | |
| 2.18 | H | CH₂OCH₃ | O | 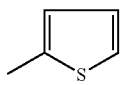 | H | |
| 2.19 | H | CH₃ | O | 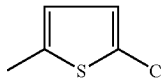 | H | |
| 2.20 | H | CH₃ | O | 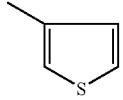 | H | |
| 2.21 | H | CH₃ | O | 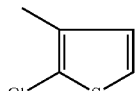 | H | |
| 2.21 | H | CH₃ | O | 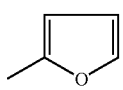 | H | |
| 2.22 | H | CH₃ | O | 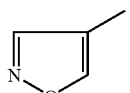 | H | |
| 2.23 | H | CH₃ | O | 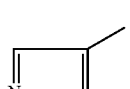 | H | resin |
| 2.24 | H | CH₂OCH₃ | O | 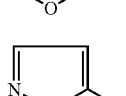 | H | |
| 2.25 | H | CH₃ | O | 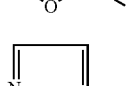 | H | |
| 2.26 | H | CH₂OCH₃ | O | 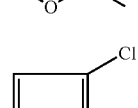 | H | |
| 2.27 | H | CH₃ | O | 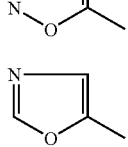 | H | |
| 2.28 | H | CH₃ | O |  | H | |

TABLE 2-continued

Compounds of the formula I, wherein A = A2 =

| Compd. No. | $R_1$ | $R_2$ | X | $R_3$ | $R_4$ | Phys. Data [m.p. ° C.] |
|---|---|---|---|---|---|---|
| 2.29 | H | $CH_3$ | O | 4-methyl-oxazol-5-yl | H | |
| 2.30 | H | $CH_3$ | O | 5-chloro-4-methyl-1,2,3-thiadiazol-4-yl | H | |
| 2.31 | H | $CH_3$ | O | pyridin-4-yl | H | |
| 2.32 | $CH_3$ | $CH_3$ | O | pyridin-4-yl | H | |
| 2.33 | H | $CH_3$ | O | 2-chloropyridin-4-yl | H | |
| 2.34 | H | $CH_2CH_3$ | O | 2-chloropyridin-4-yl | H | |
| 2.35 | H | $CH_2OCH_3$ | O | 2-chloropyridin-4-yl | H | |
| 2.36 | H | $CH_3$ | O | 2-fluoropyridin-4-yl | H | |
| 2.37 | H | $CH_3$ | O | 2-hydroxypyridin-4-yl | H | |
| 2.38 | H | $CH_3$ | O | 2-trifluoromethoxypyridin-4-yl | H | |

TABLE 2-continued

Compounds of the formula I, wherein A = A2 =

| Compd. No. | $R_1$ | $R_2$ | X | $R_3$ | $R_4$ | Phys. Data [m.p. °C.] |
|---|---|---|---|---|---|---|
| 2.39 | H | $CH_3$ | O | 3-Cl-4-methylpyridin-4-yl | H | |
| 2.40 | H | $CH_3$ | O | 3-F-4-methylpyridin-4-yl | H | resin |
| 2.41 | H | $CH_2OCH_3$ | O | 3-F-4-methylpyridin-4-yl | H | |
| 2.42 | H | $CH_3$ | O | 5-methylpyridin-3-yl | H | |
| 2.43 | H | $CH_3$ | S | 5-methylpyridin-3-yl | H | |
| 2.44 | H | $CH_3$ | O | 2-Cl-3-methylpyridin-3-yl | H | |
| 2.45 | H | $CH_3$ | O | 2-F-3-methylpyridin-3-yl | H | |
| 2.46 | H | $CH_2OCH_3$ | O | 2-F-3-methylpyridin-3-yl | H | |
| 2.47 | H | $CH_3$ | O | 2-$CF_3$-3-methylpyridin-3-yl | H | |
| 2.48 | H | $CH_3$ | O | 2-$OCF_3$-3-methylpyridin-3-yl | H | |

TABLE 2-continued

Compounds of the formula I, wherein A = A2 =

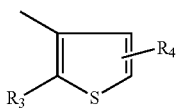

| Compd. No. | R₁ | R₂ | X | R₃ | R₄ | Phys. Data [m.p. ° C.] |
|---|---|---|---|---|---|---|
| 2.49 | H | CH₃ | O | 3-methyl-2-hydroxypyridin-yl | H | >235 |
| 2.50 | H | CH₂OCH₃ | O | 3-methyl-2-hydroxypyridin-yl | H | |
| 2.51 | H | CH₃ | O | 4-chloro-3-methylpyridin-yl | H | |
| 2.52 | H | CH₃ | O | 6-chloro-3-methylpyridin-yl | H | |
| 2.53 | H | CH₂CH₃ | O | 6-chloro-3-methylpyridin-yl | H | |
| 2.54 | H | CH₃ | O | 4-fluoro-3-methylpyridin-yl | H | |
| 2.55 | H | CH₃ | O | 6-methylpyridin-yl | H | |
| 2.56 | H | CH₃ | O | 3-chloro-2-methylpyridin-yl | H | |
| 2.57 | CH₃ | CH₃ | O | 3-chloro-2-methylpyridin-yl | H | |
| 2.58 | H | CH₃ | O | 3-fluoro-2-methylpyridin-yl | H | |

TABLE 2-continued

Compounds of the formula I, wherein A = A2 =

[Thiophene structure with methyl group, $R_3$, and $R_4$ substituents]

| Compd. No. | $R_1$ | $R_2$ | X | $R_3$ | $R_4$ | Phys. Data [m.p. ° C.] |
|---|---|---|---|---|---|---|
| 2.59 | H | CH$_3$ | O | 2-methylpyrimidin-4-yl | H | |
| 2.60 | H | CH$_3$ | O | 4-chloro-2-methylpyrimidin-5-yl | H | |
| 2.61 | H | CH$_2$CH$_3$ | O | 4-bromo-2-methylpyrimidin-5-yl | H | |
| 2.62 | H | CH$_3$ | O | 5-methylpyrazin-2-yl | H | |
| 2.63 | H | CH$_3$ | O | 3-methylpyridazin-4-yl | H | |
| 2.64 | H | CH$_3$ | O | 4-chloro-3-methylpyridazin-5-yl | H | |
| 2.65 | H | CH$_3$ | O | 5-chloro-3-methylpyridazin-4-yl | H | |
| 2.66 | H | CH$_3$ | O | 6-chloro-3-methylpyridazin-4-yl | H | |
| 2.67 | CH$_3$ | CH$_3$ | O | 6-chloro-3-methylpyridazin-4-yl | H | |

TABLE 3
Compounds of the formula I, wherein A = A17 =
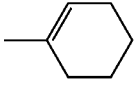
| Compd. No. | R₁ | R₂ | X | R₃₁ | R₄ | Phys. Data [m.p. ° C.] |
|---|---|---|---|---|---|---|
| 3.1 | H | CH₃ | O | 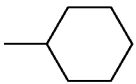 | H | |
| 3.2 | H | CH₃ | O | 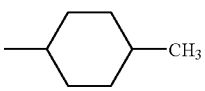 | H | |
| 3.3 | H | CH₃ | O | 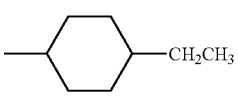 | H | |
| 3.4 | H | CH₃ | O | 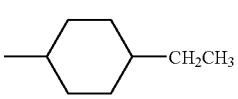 | H | |
| 3.5 | H | CH₂OCH₃ | O | 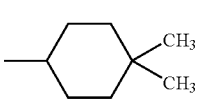 | H | |
| 3.6 | H | CH₃ | O | 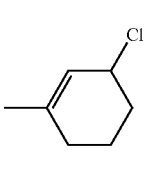 | H | |
| 3.7 | H | CH₃ | O | 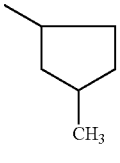 | H | |
| 3.8 | H | CH₃ | O | 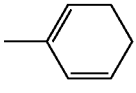 | H | |
| 3.9 | H | CH₃ | O | 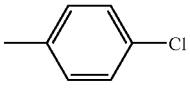 | H | |
| 3.10 | H | CH₃ | O | 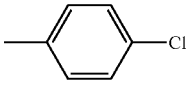 | H | |
| 3.11 | H | CH₂CH₃ | O | 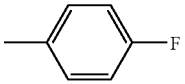 | H | |
| 3.12 | H | CH₃ | O |  | H | |

TABLE 3-continued
Compounds of the formula I, wherein A = A17 =
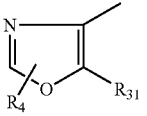
| Compd. No. | R$_1$ | R$_2$ | X | R$_{31}$ | R$_4$ | Phys. Data [m.p. ° C.] |
|---|---|---|---|---|---|---|
| 3.13 | H | CH$_3$ | O | 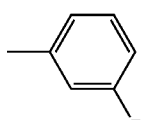 | H | |
| 3.14 | H | CH$_3$ | O | 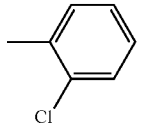 | H | |
| 3.15 | H | CH$_3$ | O | 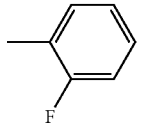 | H | |
| 3.16 | H | CH$_3$ | O | 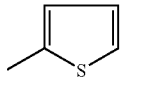 | H | |
| 3.17 | H | CH$_3$ | O | 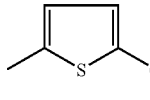 | H | |
| 3.18 | H | CH$_3$ | O | 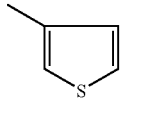 | H | |
| 3.19 | H | CH$_3$ | O | 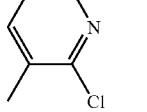 | H | |
| 3.20 | H | CH$_3$ | O | 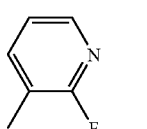 | H | |
| 3.21 | H | CH$_3$ | O | 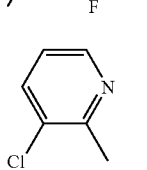 | H | |
| 3.22 | H | CH$_3$ | O |  | H | |

TABLE 3-continued

Compounds of the formula I, wherein A = A17 =

| Compd. No. | R₁ | R₂ | X | R₃₁ | R₄ | Phys. Data [m.p. ° C.] |
|---|---|---|---|---|---|---|
| 3.23 | CH₃ | CH₃ | O | 3-chloro-2-methylpyridin-yl | H | |
| 3.24 | H | CH₃ | O | 3-fluoro-2-methylpyridin-yl | H | |
| 3.25 | H | CH₃ | S | 3-fluoro-2-methylpyridin-yl | H | |

TABLE 4

Compounds of the formula I, wherein A = A21 =

| Compd. No. | R₁ | R₂ | X | R₃₁ | Phys. Data [m.p. ° C.] |
|---|---|---|---|---|---|
| 4.1 | H | CH₃ | O | cyclohex-1-en-1-yl | |
| 4.2 | H | CH₃ | O | cyclohexyl | |
| 4.3 | H | CH₃ | O | 4-methylcyclohexyl | |
| 4.4 | H | CH₃ | O | 4-ethylcyclohexyl | |
| 4.5 | H | CH₂OCH₃ | O | 4-ethylcyclohexyl | |
| 4.6 | H | CH₃ | O | 4,4-dimethylcyclohexyl | |

TABLE 4-continued

Compounds of the formula I, wherein A = A21 =

| Compd. No. | R₁ | R₂ | X | R₃₁ | Phys. Data [m.p. ° C.] |
|---|---|---|---|---|---|
| 4.7 | H | CH₃ | O | 3-chloro-6-methyl-cyclohexenyl | |
| 4.8 | H | CH₃ | O | 3-methyl-cyclopentyl | |
| 4.9 | H | CH₃ | O | cyclohexenyl | |
| 4.10 | H | CH₃ | O | 4-chlorophenyl | resin |
| 4.11 | H | CH₂CH₃ | O | 4-chlorophenyl | |
| 4.12 | H | CH₃ | O | 4-fluorophenyl | |
| 4.13 | H | CH₃ | O | 3-chlorophenyl | |
| 4.14 | H | CH₃ | O | 3-fluorophenyl | |
| 4.15 | H | CH₃ | O | 2-chlorophenyl | |
| 4.16 | H | CH₃ | O | 2-fluorophenyl | |
| 4.17 | H | CH₃ | O | 2-thienyl | |

TABLE 4-continued
Compounds of the formula I, wherein A = A21 =
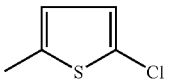
| Compd. No. | R₁ | R₂ | X | R₃₁ | Phys. Data [m.p. ° C.] |
|---|---|---|---|---|---|
| 4.18 | H | CH₃ | O | 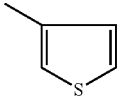 | |
| 4.19 | H | CH₃ | O | 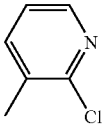 | |
| 4.20 | H | CH₃ | O | 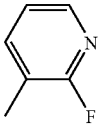 | |
| 4.21 | H | CH₃ | O | 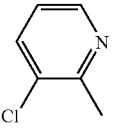 | |
| 4.22 | H | CH₃ | O | 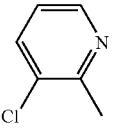 | |
| 4.23 | CH₃ | CH₃ | O | 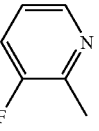 | |
| 4.24 | H | CH₃ | O | 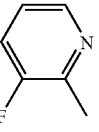 | |
| 4.25 | H | CH₃ | S |  | |

TABLE 5

Compounds of the formula I, wherein A = A24 =

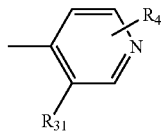

| Compd. No. | R₁ | R₂ | X | R₃₁ | R₄ | Phys. Data [m.p. ° C.] |
|---|---|---|---|---|---|---|
| 5.1 | H | CH₃ | O | cyclohexenyl | H | |
| 5.2 | H | CH₃ | O | cyclohexyl | H | |
| 5.3 | H | CH₃ | O | 4-methylcyclohexyl | H | |
| 5.4 | H | CH₃ | O | 4-ethylcyclohexyl | H | |
| 5.5 | H | CH₂OCH₃ | O | 4-ethylcyclohexyl | H | |
| 5.6 | H | CH₃ | O | 4,4-dimethylcyclohexyl | H | |
| 5.7 | H | CH₃ | O | 6-chlorocyclohex-1-enyl | H | |
| 5.8 | H | CH₃ | O | 3-methylcyclopentyl | H | |
| 5.9 | H | CH₃ | O | cyclohexa-1,3-dienyl | H | |
| 5.10 | H | CH₃ | O | 4-chlorophenyl | H | |
| 5.11 | H | CH₂CH₃ | O | 4-chlorophenyl | H | |
| 5.12 | H | CH₃ | O | 4-fluorophenyl | H | resin |

TABLE 5-continued

Compounds of the formula I, wherein A = A24 =

| Compd. No. | R₁ | R₂ | X | R₃₁ | R₄ | Phys. Data [m.p. °C.] |
|---|---|---|---|---|---|---|
| 5.13 | H | CH₃ | O | 3-chlorophenyl | H | |
| 5.14 | H | CH₃ | O | 3-fluorophenyl | H | |
| 5.15 | H | CH₃ | O | 2-chlorophenyl | H | |
| 5.16 | H | CH₃ | O | 2-fluorophenyl | H | |
| 5.17 | H | CH₃ | O | thien-2-yl | H | |
| 5.18 | H | CH₃ | O | 5-chlorothien-2-yl | H | |
| 5.19 | H | CH₃ | O | thien-3-yl | H | |
| 5.20 | H | CH₃ | O | 2-chloropyridin-3-yl | H | |
| 5.21 | H | CH₃ | O | 2-fluoropyridin-3-yl | H | |
| 5.22 | H | CH₃ | O | 3-chloropyridin-2-yl | H | |

TABLE 5-continued
Compounds of the formula I, wherein A = A24 =
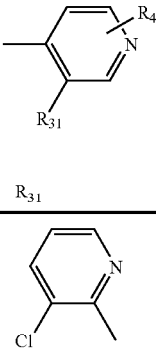
| Compd. No. | R₁ | R₂ | X | R₃₁ | R₄ | Phys. Data [m.p. ° C.] |
|---|---|---|---|---|---|---|
| 5.23 | CH₃ | CH₃ | O |  | H | |
| 5.24 | H | CH₃ | O | 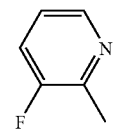 | H | |
| 5.25 | H | CH₃ | S | 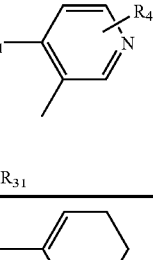 | H | |
TABLE 6
Compounds of formula I, wherein A = A25 =
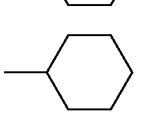
| Compd. No. | R₁ | R₂ | X | R₃₁ | R₄ | Phys. Data [m.p. ° C.] |
|---|---|---|---|---|---|---|
| 6.1 | H | CH₃ | O | 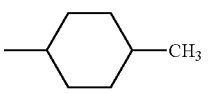 | H | |
| 6.2 | H | CH₃ | O | 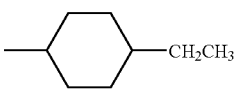 | H | |
| 6.3 | H | CH₃ | O | 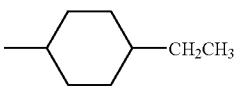—CH₃ | H | |
| 6.4 | H | CH₃ | O | —CH₂CH₃ | H | |
| 6.5 | H | CH₂OCH₃ | O | —CH₂CH₃ | H | |
| 6.6 | H | CH₃ | O | 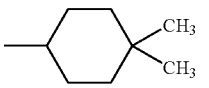 | H | |

TABLE 6-continued
Compounds of formula I, wherein A = A25 =
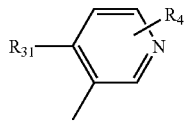
| Compd. No. | R₁ | R₂ | X | R₃₁ | R₄ | Phys. Data [m.p. ° C.] |
|---|---|---|---|---|---|---|
| 6.7 | H | CH₃ | O | 3-chloro-cyclohexenyl | H | |
| 6.8 | H | CH₃ | O | 3-methyl-cyclopentyl | H | |
| 6.9 | H | CH₃ | O | cyclohexenyl | H | |
| 6.10 | H | CH₃ | O | 4-Cl-phenyl | H | 178–180 |
| 6.11 | H | CH₂CH₃ | O | 4-Cl-phenyl | H | |
| 6.12 | H | CH₂OCH₃ | O | 4-Cl-phenyl | H | |
| 6.13 | H | CH₃ | O | 4-OCF₃-phenyl | H | |
| 6.14 | H | CH₃ | O | 4-CF₃-phenyl | H | |
| 6.15 | H | CH₃ | O | 4-F-phenyl | H | 165–167 |
| 6.16 | H | CH₃ | S | 4-F-phenyl | H | |
| 6.17 | H | CH₃ | O | 4-F-phenyl | H | |
| 6.18 | H | CH₃ | O | 3-Cl-phenyl | H | |

TABLE 6-continued
Compounds of formula I, wherein A = A25 =
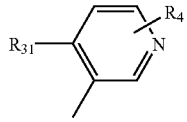
| Compd. No. | R₁ | R₂ | X | R₃₁ | R₄ | Phys. Data [m.p. ° C.] |
|---|---|---|---|---|---|---|
| 6.19 | H | CH₃ | O | 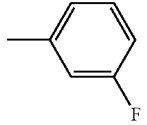 | H | |
| 6.20 | H | CH₃ | O | 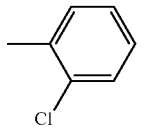 | H | |
| 6.21 | H | CH₃ | O | 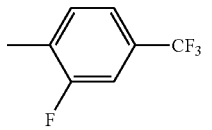 | H | |
| 6.22 | H | CH₃ | O | 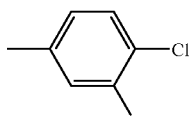 | H | |
| 6.23 | H | CH₃ | O | 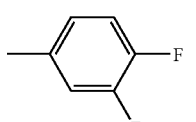 | H | |
| 6.24 | H | CH₃ | O | 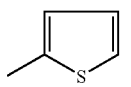 | H | |
| 6.25 | H | CH₃ | O | 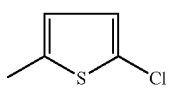 | H | |
| 6.26 | H | CH₃ | O | 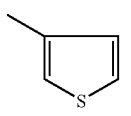 | H | |
| 6.27 | H | CH₃ | O | 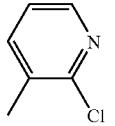 | H | |
| 6.28 | H | CH₃ | O |  | H | |

TABLE 6-continued
Compounds of formula I, wherein A = A25 =
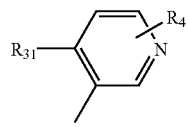
| Compd. No. | R₁ | R₂ | X | R₃₁ | R₄ | Phys. Data [m.p. ° C.] |
|---|---|---|---|---|---|---|
| 6.29 | H | CH₃ | O | 3-methyl-2-fluoropyridin-4-yl | H | |
| 6.30 | H | CH₃ | O | 3-chloro-2-methylpyridin-4-yl | H | |
| 6.31 | CH₃ | CH₃ | O | 3-chloro-2-methylpyridin-4-yl | H | |
| 6.32 | H | CH₃ | O | 3-fluoro-2-methylpyridin-4-yl | H | |
| 6.33 | H | CH₃ | S | 3-fluoro-2-methylpyridin-4-yl | H | |
| 6.34 | H | CH₃ | O | 5-fluoro-6-methylpyridin-3-yl | H | |
| 6.35 | H | CH₃ | O | 5-chloro-6-methylpyridin-3-yl | H | |

TABLE 7
Compounds of the formula I, wherein A = A26 =
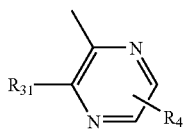
| Compd. No. | R₁ | R₂ | X | R₃₁ | R₄ | phys. data m.p. ° C. |
|---|---|---|---|---|---|---|
| 7.1 | H | CH₃ | O | phenyl | H | |
| 7.2 | H | CH₃ | O | 4-Cl-phenyl | H | resin |
| 7.3 | H | CH₂CH₃ | O | 4-Cl-phenyl | H | |
| 7.4 | H | CH₂OCH₃ | O | 4-Cl-phenyl | H | |
| 7.5 | H | CH₃ | O | 4-F-phenyl | H | |
| 7.6 | H | CH₂OCH₃ | O | 4-F-phenyl | H | |
| 7.7 | H | CH₃ | S | 4-F-phenyl | H | |
| 7.8 | H | CH₃ | O | 3,4-diCl-phenyl | H | |
| 7.9 | H | CH₃ | O | 3,4-diF-phenyl | H | |
| 7.10 | CH₃ | CH₃ | O | 3,4-diF-phenyl | H | |
| 7.11 | H | CH₃ | O | 4-CF₃-phenyl | H | |
| 7.12 | H | CH₃ | O | 4-OCF₃-phenyl | H | |

TABLE 7-continued
Compounds of the formula I, wherein A = A26 =
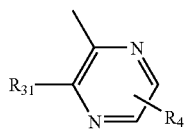
| Compd. No. | R₁ | R₂ | X | R₃₁ | R₄ | phys. data m.p. ° C. |
|---|---|---|---|---|---|---|
| 7.13 | H | CH₃ | O | 3-CF₃-phenyl | H | |
| 7.14 | H | CH₃ | O | 2-Cl-3-methylthiophene | H | |
| 7.15 | H | CH₃ | O | 3-Cl-2-methylthiophene | H | |
TABLE 8
Compounds of the formula I, wherein A = A27 =
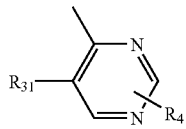
| Compd. No. | R₁ | R₂ | X | R₃₁ | R₄ | phys. data m.p. ° C. |
|---|---|---|---|---|---|---|
| 8.1 | H | CH₃ | O | phenyl | H | 63–65 |
| 8.2 | H | CH₃ | O | 4-Cl-phenyl | H | 156–157 |
| 8.3 | H | CH₂CH₃ | O | 4-Cl-phenyl | H | |
| 8.4 | H | CH₂OCH₃ | O | 4-Cl-phenyl | H | |
| 8.5 | H | CH₃ | O | 4-F-phenyl | H | 119–122 |
| 8.6 | H | CH₂OCH₃ | O | 4-F-phenyl | H | |

TABLE 8-continued
Compounds of the formula I, wherein A = A27 =
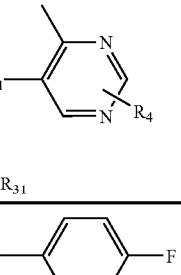
| Compd. No. | R₁ | R₂ | X | R₃₁ | R₄ | phys. data m.p. °C. |
|---|---|---|---|---|---|---|
| 8.7 | H | CH₃ | S | 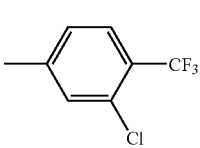 4-F-C₆H₄ | H | |
| 8.8 | H | CH₃ | O | 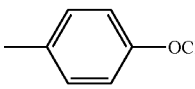 3-Cl-4-CF₃-C₆H₃ | H | |
| 8.9 | H | CH₃ | O | 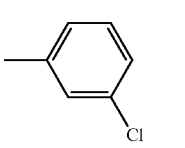 4-OCF₃-C₆H₄ | H | |
| 8.10 | CH₃ | CH₃ | O | 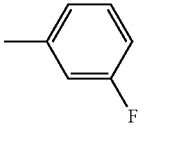 3-Cl-C₆H₄ | H | |
| 8.11 | H | CH₃ | O | 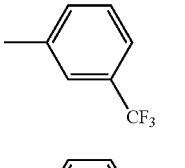 3-F-C₆H₄ | H | |
| 8.12 | H | CH₃ | O | 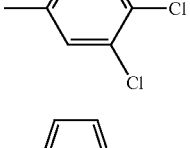 3-CF₃-C₆H₄ | H | |
| 8.13 | H | CH₃ | O | 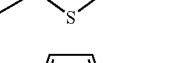 3,4-Cl₂-C₆H₃ | H | |
| 8.14 | H | CH₃ | O | 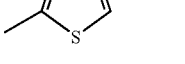 2-thienyl | H | 159–161 |
| 8.15 | H | CH₂OCH₃ | O | 2-thienyl | H | 139–141 |
| 8.16 | H | CH₃ | O | 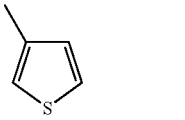 3-thienyl | H | 140–143 |
| 8.17 | H | CH₃ | O | 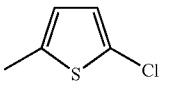 5-Cl-2-thienyl | H | |

TABLE 8-continued

Compounds of the formula I, wherein A = A27 =

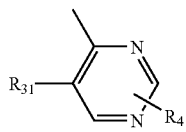

| Compd. No. | $R_1$ | $R_2$ | X | $R_{31}$ | $R_4$ | phys. data m.p. ° C. |
|---|---|---|---|---|---|---|
| 8.18 | H | $CH_3$ | O | 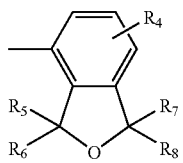 | H | |

TABLE 9

Compounds of the formula I, wherein A = A31 =

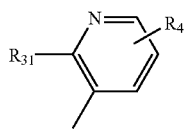

| Compd. No. | $R_1$ | $R_2$ | X | $R_4$ | $R_5$ | $R_6$ | $R_7$ | $R_8$ | phys.data m.p. ° C. |
|---|---|---|---|---|---|---|---|---|---|
| 9.1 | H | $CH_3$ | O | H | H | $CH_3$ | $CH_3$ | $CH_3$ | 165–167 |
| 9.2 | H | $CH_2CH_3$ | O | H | H | $CH_3$ | $CH_3$ | $CH_3$ | |
| 9.3 | H | $CH_2OCH_3$ | O | H | H | $CH_3$ | $CH_3$ | $CH_3$ | oil; MS |
| 9.4 | $CH_3$ | $CH_3$ | O | H | H | $CH_3$ | $CH_3$ | $CH_3$ | |
| 9.5 | H | $CH_3$ | S | H | H | $CH_3$ | $CH_3$ | $CH_3$ | |
| 9.6 | H | $CH_3$ | O | H | $CH_3$ | $CH_3$ | $CH_3$ | H | |
| 9.7 | H | $CH_2OCH_3$ | O | H | $CH_3$ | $CH_3$ | $CH_3$ | H | |

TABLE 10

Compounds of formula I, wherein A = A22 =

| Compd. No. | $R_1$ | $R_2$ | X | $R_{31}$ | $R_4$ | Phys. Data [m.p. ° C.] |
|---|---|---|---|---|---|---|
| 10.1 | H | $CH_3$ | O | (cyclohexenyl) | H | |
| 10.2 | H | $CH_3$ | O | (cyclohexyl) | H | |

TABLE 10-continued
Compounds of formula I, wherein A = A22 =
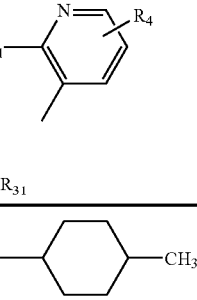
| Compd. No. | $R_1$ | $R_2$ | X | $R_{31}$ | $R_4$ | Phys. Data [m.p. ° C.] |
|---|---|---|---|---|---|---|
| 10.3 | H | $CH_3$ | O | 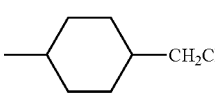 | H | oil |
| 10.4 | H | $CH_3$ | O | 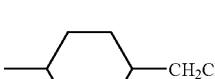 | H | |
| 10.5 | H | $CH_2OCH_3$ | O | 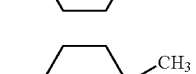 | H | |
| 10.6 | H | $CH_3$ | O | 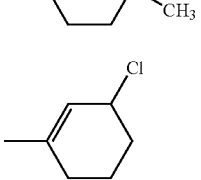 | H | |
| 10.7 | H | $CH_3$ | O | 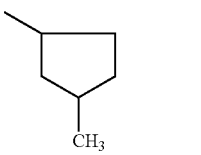 | H | |
| 10.8 | H | $CH_3$ | O | 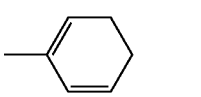 | H | |
| 10.9 | H | $CH_3$ | O | 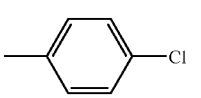 | H | |
| 10.10 | H | $CH_3$ | O | 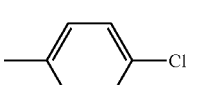 | H | |
| 10.11 | H | $CH_2CH_3$ | O | 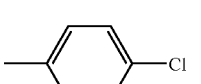 | H | |
| 10.12 | H | $CH_2OCH_3$ | O | 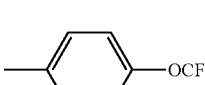 | H | |
| 10.13 | H | $CH_3$ | O | 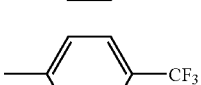 | H | |
| 10.14 | H | $CH_3$ | O |  | H | |

TABLE 10-continued

Compounds of formula I, wherein A = A22 =

| Compd. No. | R₁ | R₂ | X | R₃₁ | R₄ | Phys. Data [m.p. ° C.] |
|---|---|---|---|---|---|---|
| 10.15 | H | CH₃ | O | 4-F-phenyl | H | 216–219 |
| 10.16 | H | CH₃ | S | 4-F-phenyl | H | |
| 10.17 | H | CH₃ | O | 4-F-phenyl | H | |
| 10.18 | H | CH₃ | O | 3-Cl-phenyl | H | |
| 10.19 | H | CH₃ | O | 3-F-phenyl | H | |
| 10.20 | H | CH₃ | O | 2-Cl-phenyl | H | |
| 10.21 | H | CH₃ | O | 2-F-phenyl | H | |
| 10.22 | H | CH₃ | O | 3-F-4-CF₃-phenyl | H | |
| 10.23 | H | CH₃ | O | 3,4-diCl-phenyl | H | |
| 10.24 | H | CH₃ | O | 3,4-diF-phenyl | H | |
| 10.25 | H | CH₃ | O | 2-thienyl | H | |

TABLE 10-continued
Compounds of formula I, wherein A = A22 =
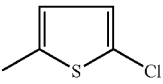
| Compd. No. | R₁ | R₂ | X | R₃₁ | R₄ | Phys. Data [m.p. ° C.] |
|---|---|---|---|---|---|---|
| 10.26 | H | CH₃ | O | 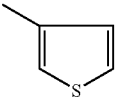 | H | |
| 10.27 | H | CH₃ | O | 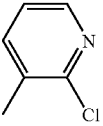 | H | |
| 10.28 | H | CH₃ | O | 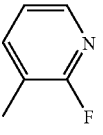 | H | |
| 10.29 | H | CH₃ | O | 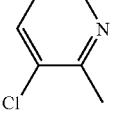 | H | |
| 10.30 | H | CH₃ | O | 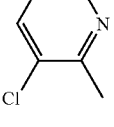 | H | |
| 10.31 | CH₃ | CH₃ | O | 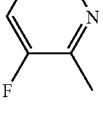 | H | |
| 10.32 | H | CH₃ | O | 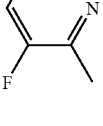 | H | |
| 10.33 | H | CH₃ | S | 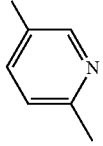 | H | |
| 10.34 | H | CH₃ | O |  | H | |

TABLE 10-continued

Compounds of formula I, wherein A = A22 =

| Compd. No. | $R_1$ | $R_2$ | X | $R_{31}$ | $R_4$ | Phys. Data [m.p. ° C.] |
|---|---|---|---|---|---|---|
| 10.35 | H | $CH_3$ | O | Cl-(pyridyl) | H | |

FORMULATION EXAMPLES FOR COMPOUNDS OF FORMULA I

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

Example B-1

Action Against *Puccinia Recondita*/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation. Compounds of Tables 1 to 10 show good activity in these tests. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-2

Action Against *Podosphaera Leucotricha*/Apple (Powdery Mildew on Apple)

5 week old apple seedlings cv. Mcintosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r. h. under a light regime of 14/10 h (light/dark) the disease incidence is assessed.

Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-3

Action Against *Venturia Inaegualis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r. h. the plants are placed for 4 days at 21° C. and 60% r. h. in a greenhouse. After another 4 day incubation period at 21° C. and 95% r. h. the disease incidence is assessed.

Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-4

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed.

Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-5

Action Against *Botrytis cinerea*/Apple (Botrytis on Apple Fruits)

In an apple fruit cv. Golden Delicious 3 holes are drilled and each filled with 30 μl droplets of the formulated test compound (0.002% active ingredient). Two hours after application 50 μl of a spore suspension of *B. cinerea* ($4\times10^5$ conidia/ml) are pipetted on the application sites. After an incubation period of 7 days at 22° C. in a growth chamber the disease incidence is assessed.

Compounds of Tables 1 to 10 show good activity in this test. The compounds 1.11, 1.15, 1.16, 1,19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-6

Action Against *Botrytis cinerea*/Grape (*Botrytis* on Grapes)

5 week old grape seedlings cv. Gutedel are treated with the formulated test compound (0.002% active ingredient) in a spray chamber. Two days after application grape plants are inoculated by spraying a spore suspension ($1\times10^6$ conidia/ml) on the test plants. After an incubation period of 4 days at 21° C. and 95% r. h. in a greenhouse the disease incidence is assessed.

Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-7

Action Against *Botrytis Cinerea*/Tomato (*Botrytis* on Tomatoes)

4 week old tomato plants cv. Roter Gnom are treated with the formulated test compound (0.002% active ingredient) in a spray chamber. Two days after application tomato plants are inoculated by spraying a spore suspension ($1\times10^5$ conidia/ml) on the test plants. After an incubation period of 4 days at 20° C. and 95% r. h. in a growth chamber the disease incidence is assessed.

Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-8

Action Against *Pyrenophora Teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3\times10^4$ conidia/ml) on the test plants. After an incubation period of 2 days at 20° C. and 95% r. h. plants are kept for 2 days at 20° C. and 60% r.h. in a greenhouse. The disease incidence is assessed 4 days after inoculation. Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

Example B-9

Action Against *Septoria Nodorum*/Wheat (Septoria Leaf Spot on Wheat)

1 week old wheat plants cv. Arina are treated with the formulated test compound (0.02% active ingredient) in a spray chamber. One day after application wheat plants are inoculated by spraying a spore suspension ($5\times10^5$ conidia/ml) on the test plants. After an incubation period of 1 day at 20° C. and 95% r. h. plants are kept for 10 days at 20° C. and 60% r.h. in a greenhouse. The disease incidence is assessed 11 days after inoculation. Compounds of Tables 1 to 10 show good activity in this test. The compounds 1.11, 1.15, 1.16, 1.19–1.21, 1.23–1.26, 1.40, 1.42, 1.49, 1.66–1.69, 1.74, 1.75, 1.81, 2.12, 2.23, 2.40, 2.49, 4.10, 5.12, 6.10, 6.15, 7.2, 8.1, 8.2, 8.5, 8.14–8.16, 10.3 and 10.15 exhibit strong efficacy (<20% infestation).

What is claimed is:

1. A trifluoromethylpyrrolcarboxamide of the formula I

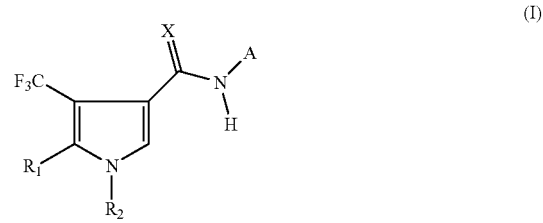

(I)

wherein

X is oxygen or sulfur;

$R_1$ is hydrogen, $C_1$–$C_4$alkyl unsubstituted or substituted, or halogen;

$R_2$ is $C_1$–$C_4$alkyl unsubstituted or substituted; and

A is

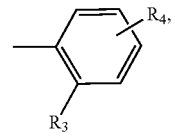

and wherein $R_3$ is pyridyl, which is unsubstituted or substituted by halogen, $C_1$–$C_6$haloalkyl, $C_1$–$C_6$alkyl, hydroxy, cyano, nitro, CHO, $C_1$–$C_4$alkoxy-$C_1$–$C_4$alkyl, COOC$_1$–$C_4$alkyl, $C_1$–$C_6$haloalkoxy-$C_1$–$C_4$alkyl, $C_1$–$C_6$alkoxy or $C_1$–$C_6$haloalkoxy; and $R_4$ is hydrogen; cyano; nitro; halogen; $C_1$–$C_4$alkoxy; $C_1$–$C_4$haloalkyl; $C_1$–$C_4$alkyl; $C_1$–$C_4$alkoxy-$C_1$–$C_4$alkyl; $C_5$–$C_7$cycloalkyl unsubstituted or substituted by $C_1$–$C_3$alkyl or $C_1$–$C_3$haloalkyl; $C_1$–$C_4$haloalkoxy-$C_1$–$C_4$alkyl; or $C_1$–$C_4$haloalkoxy.

2. A compound of formula I according to claim 1, wherein X is oxygen.

3. A compound of formula I according to claim 1, wherein X is sulfur.

4. A compound of formula I according to claim 2, wherein
$R_1$ is hydrogen, $C_1$–$C_4$alkyl or $C_1$–$C_4$haloalkyl;
$R_2$ is $C_1$–$C_4$alkyl, $C_1$–$C_3$haloalkyl or $C_1$–$C_3$alkoxy-$C_1$–$C_3$alkyl;
$R_3$ is pyridyl, which is unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy; and
$R_4$ is hydrogen; halogen; $C_1$–$C_4$alkyl; $C_1$–$C_4$alkoxy; $C_5$–$C_7$cycloalkyl unsubstituted or substituted by $C_1$–$C_3$alkyl or $C_1$–$C_3$haloalkyl; $C_1$–$C_4$haloalkyl; or $C_1$–$C_4$haloalkoxy.

5. A compound of formula I according to claim 4, wherein
$R_1$ is hydrogen or $C_1$–$C_3$alkyl;
$R_2$ is $C_1$–$C_3$alkyl or $C_1$–$C_3$alkoxy-$C_1$–$C_3$alkyl;
$R_3$ is pyridyl, which is unsubstituted or substituted by halogen, $C_1$–$C_4$alkyl, $C_1$–$C_4$haloalkyl or $C_1$–$C_4$haloalkoxy; and
$R_4$ is hydrogen; halogen; $C_1$–$C_3$alkyl; $C_1$–$C_3$haloalkyl; $C_5$–$C_7$cycloalkyl unsubstituted or substituted by $C_1$–$C_3$alkyl or $C_1$–$C_3$haloalkyl; $C_1$–$C_3$alkoxy; or $C_1$–$C_3$haloalkoxy.

6. A compound of formula I according to claim 3, wherein
$R_1$ is hydrogen, $C_1$–$C_4$alkyl or $C_1$–$C_4$haloalkyl;
$R_2$ is $C_1$–$C_4$alkyl, $C_1$–$C_3$haloalkyl or $C_1$–$C_3$alkoxy-$C_{-1}$–$C_3$alkyl;
$R_3$ is pyridyl, which is unsubstituted or substituted by halogen, hydroxy, $C_1$–$C_4$alkyl, $C_1$–$C_4$haloalkyl, $C_1$–$C_4$alkoxy or $C_1$–$C_4$haloalkoxy; and
$R_4$ is hydrogen; halogen; $C_1$–$C_4$alkyl; $C_1$–$C_4$alkoxy; $C_5$–$C_7$cycloalkyl unsubstituted or substituted by $C_1$–$C_3$alkyl or $C_1$–$C_3$haloalkyl; $C_1$–$C_4$haloalkyl; or $C_1$–$C_4$haloalkoxy.

7. A compound of formula I according to claim 6, wherein
$R_1$ is hydrogen or $C_1$–$C_3$alkyl;
$R_2$ is $C_1$–$C_3$alkyl or $C_1$–$C_3$alkoxy-$C_1$–$C_3$alkyl;
$R_3$ is, pyridyl, which is unsubstituted or substituted by halogen, $C_1$–$C_4$alkyl, $C_1$–$C_4$haloalkyl or $C_1$–$C_4$haloalkoxy; and
$R_4$ is hydrogen; halogen; $C_1$–$C_3$alkyl; $C_1$–$C_3$haloalkyl; $C_5$–$C_7$cycloalkyl unsubstituted or substituted by $C_1$–$C_3$alkyl or $C_1$–$C_3$haloalkyl; $C_1$–$C_3$alkoxy; or $C_1$–$C_3$haloalkoxy.

8. A process for the preparation of compounds of formula I which comprises reacting the starting materials according to the scheme

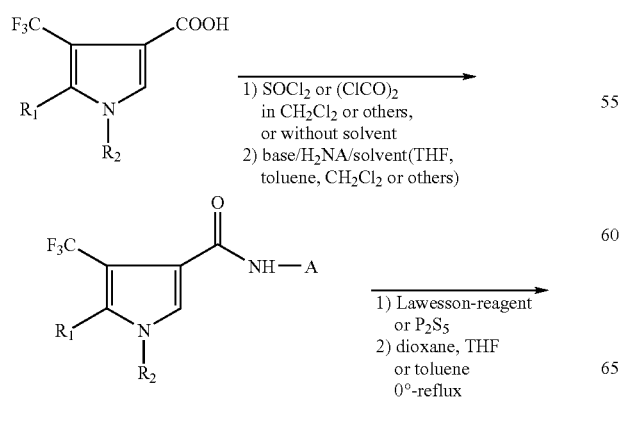

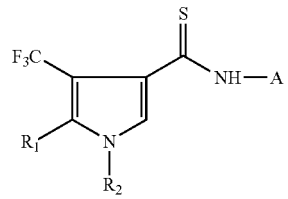

Base = $NEt_3$, Hünig-base, $Na_2CO_3$, $K_2CO_3$ and others wherein $R_1$, $R_2$ and A are as defined for formula I in claim 1; or when A is phenyl, pyridine or pyrimidine according to the scheme

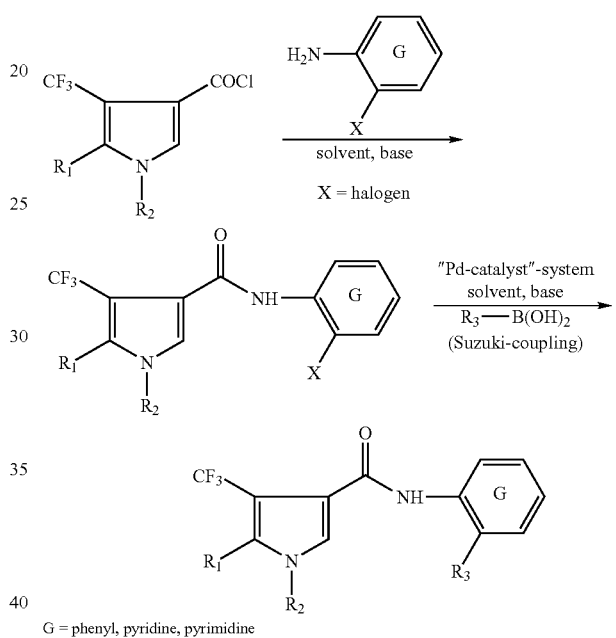

G = phenyl, pyridine, pyrimidine wherein $R_1$, $R_2$ and $R_3$ are as defined for formula I in claim 1.

9. A composition for controlling microorganisms and preventing attack and infestation of plants therewith, said composition comprising:

(A) an active ingredient having the general formula:

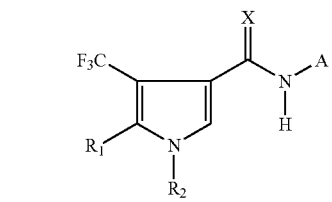

wherein
X is oxygen or sulfur;
$R_1$ is hydrogen, $C_1$–$C_4$alkyl unsubstituted or substituted, or halogen;
$R_2$ is $C_1$–$C_4$alkyl unsubstituted or substituted; and
A is

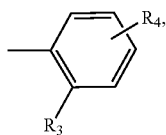

and wherein $R_3$ is pyridyl, which is unsubstituted or substituted by halogen, $C_1$–$C_6$haloalkyl, $C_1$–$C_6$alkyl, hydroxy, cyano, nitro, CHO, $C_1$–$C_4$alkoxy-$C_1$–$C_4$alkyl, COO$C_1$–$C_4$alkyl, $C_1$–$C_6$haloalkoxy-$C_1$–$C_4$alkyl, $C_1$–$C_6$alkoxy or $C_1$–$C_6$haloalkoxy; and $R_4$ is hydrogen; cyano; nitro; halogen; $C_1$–$C_4$alkoxy; $C_1$–$C_4$haloalkyl; $C_1$–$C_4$alkyl; $C_1$–$C_4$alkoxy-$C_1$–$C_4$alkyl; $C_5$–$C_7$cycloalkyl unsubstituted or substituted by $C_1$–$C_3$alkyl or $C_1$–$C_3$haloalkyl; $C_1$–$C_4$haloalkoxy-$C_1$–$C_4$alkyl; or $C_1$–$C_4$haloalkoxy; and (B) a suitable carrier.

10. A method for ptotecting plants against infestation by phytopathogenic microorganisms by application of a compound of formula I according to claim 1.

11. A method of controlling or preventing infestation of cultivated plants by phytopathogenic microorganisms by application of a compound of formula I as claimed in claim 1 to plants, to parts thereof or the locus thereof.

* * * * *